(12) United States Patent
Cheng et al.

(10) Patent No.: US 10,036,041 B2
(45) Date of Patent: Jul. 31, 2018

(54) METHOD FOR POSITIONING AND INTEGRATING TRANSGENE AND USE THEREOF

(71) Applicants: SHANGHAI GENON BIOENGINEERING CO., LTD, Shanghai (CN); SHANGHAI TRANSGENIC RESEARCH CENTER, Shanghai (CN)

(72) Inventors: Guoxiang Cheng, Shanghai (CN); Jianquan Chen, Shanghai (CN); Siguo Liu, Shanghai (CN)

(73) Assignees: SHANGHAI GENON BIOENGINEERING CO., LTD, Shanghai (CN); SHANGHAI TRANSGENIC RESEARCH CENTER, Shanghai (CN)

( * ) Notice: Subject to any disclaimer, the term of this patent is extended or adjusted under 35 U.S.C. 154(b) by 0 days.

(21) Appl. No.: 15/024,405

(22) PCT Filed: Sep. 28, 2013

(86) PCT No.: PCT/CN2013/084554
§ 371 (c)(1),
(2) Date: Jun. 24, 2016

(87) PCT Pub. No.: WO2015/042895
PCT Pub. Date: Apr. 2, 2015

(65) Prior Publication Data
US 2016/0304906 A1    Oct. 20, 2016

(51) Int. Cl.
*C12N 15/00* (2006.01)
*C07H 21/04* (2006.01)
*C12N 15/90* (2006.01)
*A01K 67/027* (2006.01)
*C12N 15/85* (2006.01)

(52) U.S. Cl.
CPC ........ *C12N 15/907* (2013.01); *A01K 67/0275* (2013.01); *C12N 15/8509* (2013.01); *A01K 2217/072* (2013.01); *A01K 2227/102* (2013.01); *A01K 2267/03* (2013.01); *C12N 2800/30* (2013.01); *C12N 2800/80* (2013.01)

(58) Field of Classification Search
None
See application file for complete search history.

(56) References Cited

FOREIGN PATENT DOCUMENTS

| CN | 1502694 A | 6/2004 |
|----|-----------|--------|
| CN | ZL200510110772 | 11/2005 |
| CN | 101603045 | 6/2008 |
| CN | 101603045 A | * 12/2009 |
| CN | 103361342 A | 10/2013 |

OTHER PUBLICATIONS

Cheng et al. machine translation for CN101603045A.*
Yuanyuan Xu et al., Excision of selectable genes from transgenic goat cells by a protein transducible TAT-Cre recombinase; Gene 419 (2008) 70-74.
"Mutually exclusive recombination of wild-type and mutant loxP sites in vivo facilitates transposon-mediated deletions from both ends of genomic DNA in PACs". Nucleic Acids Research, vol. 32 No. 18; 5668-5676 Nucleic Acids Research, 2004, vol. 32, No. 18; doi:10.1093/nar/gkh900.
"Excision of selectable genes from transgenic goat cells by a protein transducible TAT-Cre recombinase"; Gene 419 (2008) 70-74.

* cited by examiner

*Primary Examiner* — Janice Li
(74) *Attorney, Agent, or Firm* — Adam Warwick Bell; Matthew Rupert Kaser

(57) ABSTRACT

Provided in the present invention is a method for positioning and integrating transgene and a use thereof. Specifically provided is a variant loxP element. The sequence "ATAAT" of an reverse repeated sequence in a wild type loxp locus is mutated into "CACCT", i.e., a variant loxp element. Also provided in the present invention are a construct comprising the variant loxP element, a vector or host cell comprising the construct and a method for preparing a transgenic animal using the vector and the host cell.

10 Claims, 18 Drawing Sheets

AGT GAATTC ATAACTTCGTATAATGTATGCTATACGAAAGGTG-G-CCGCGG
    EcoRI                    loxp sequence                    Sac I
GA GTCGAC CAT GGCGGCCGC CT ATAACTTCGTATAATGTATGCTATACGA
   Sal I         Not I                     loxp sequence
AGTTAT GC AAGCTT GG      (SEQ ID NO: 39)
        Hind III CTCGAG ATGAAGGTCCTCATCCTTGCCTGTCTGGTGGCTCTGGCCAT
 Xho I                 secreting peptide of β-casein
TGCA CACCACCACCACCACCAC AGAAGAAGAAGAAAG TGCAGCA
         6×His tag              enterokinase cleavage site
ACCTGAGCACCTGCGTGCTGGGCAAGCTGAGCCAGGAGCTGCACAA
                    encoding sequence of salmon calcitonin
GCTGCAGACCTACCCCGTGACCAACACCGGCAGCGGCACCCCCGGC TAA CTCGAG     (SEQ ID NO.: 40)
    Xho I

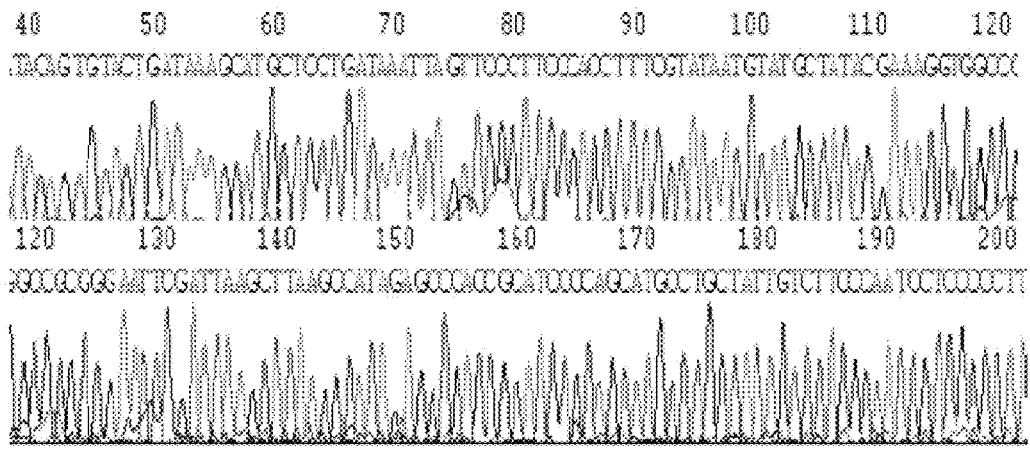
Figure 19
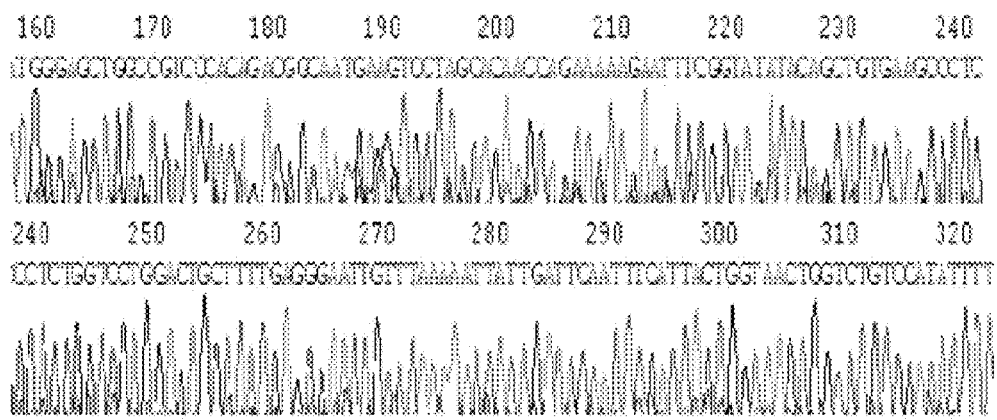
Figure 20
Figure 21

TTCTCGAAACAAGCGCACCAAGAAACCTTCCATTCTACGAGCGCCTGGGCTTCACCGTGACCGCCGA
TGTCGAGGTGCCCGAGGGACCTAGGACCTGGTGTATGACACGAAAACCTGGCGCCTAATGATCTAG
AACCGGTCATGGCCGCAATAAAATATCTTTATTTTCATTACATCTGTGTGTTGGTTTTTTGTGTGTTC
GAACTAGATGCTGTCGACCGATGCGGCCGCCTATAACTTCGTATAATGTATGCTATACGAAGTTATT
AGGTCTGAAGAGGAGTTTACGTCCAGCCAAGCTAATGGGAGCTGGCCGTccacagacggcaatgaagtcctagc
acaaccagaaaagaagttcggtagatacagctgtgaagccctctggtcctgactgctttgagggaattgtttaaaaattattgattcaattcattactggtaact
ggtctgtccatatttctattcttcctggctcagtcttgggtttgtacatgtctggaatgtatccgtttcttctgggttgtcctttattagacatgtgtggggggcacac
agcaccgaccagtgagactcataccggcttcctggggccaggatgcgggccccaagcagcacggcatcctagactgtgtgaatgccactgacctgcccag
cccacagttcattctgagagaagtgattcttgcttctgcacttacaggccaagacctgacctgctctgaagagcagggggtttggcaggagggggagatgc
tgagagccgatggggtccaggtctcctcccaggtccactctctggggcagcgcttggaaaagattgtccagcctccctccccatagtggtcagtgccagctgc
cccaggccagaggtgctttattttccgtctctctctctgatggtattctctggaagctgaaggttcctggaagttatgaatagcttgccatgaaggcatggttgtg
gtcatggttcacaggaactgggagacccctgcagctcgggacgtcctgaggttggtggcaccctgattcctaagctcgctgggaacggggtgctactctctcct
ggctgacctccctctgctctgcatcaccccagttctgagagcagagtggtgctggggcacagccctctgcatctgacactgtgtcaaaccaccatgctggtgt
tcgggggggccacctatgggaaggctctcactgcaggggtgccctgtccctgagagatcagaagtccagtctggatgtcgaatggccgagctcctcca
gaggctccaggaggatcctgcccctccgccgcggccccagctcctggtgccgcacccttgggccgatctcgtagaagcctcagtccagtctctgcctc
cgtgttcactggcattctcccatgtccctctgtgtccccgttttctcacaaggacaccggacataagattagccccgttccagcatcctgatcacctgcatcaca
tctgtaaagacctagattccaaacaagatccatcctgaagttcctggtggacgtgagttctggagcgacgccttcaacccatcacagcttgcggttcatcgcaa
aacacggaacctggatttatcgtaaaaccaggtcttcgtgaaacactgagcttcgaggcttgttgcaagaattaaaggtgctaatacagatcagggcangga
ccgaagctggccaagcctcctcttccatcacaggaaagggaggtctggggcggccgggggtctgctccgtgggtggctctttctggtacagtcaccaac
agtctctccgggaaggaaccagaggccagagagccaagccagagctagtctaggagatccctgagcctccacccaagatgccgaccaggccagcggccc
cctggaaagaccctacagtctaggggggaatcaggagccgaccctgccaggccccgctatcaggagaccaccccaccctgctcctgttccctacccccagta
cgcccaccgaccctgagatgagtggttactgcttagaatgtcaattgaaggcttttgtacccccttgccagtggcacagggcaccacagccccgctgggta
ctgatgcccatgtggactcagccaggaggactgtcctgcgcctccctgctcgggccccctccatactcagcgacacaccccagcaccagcattcccaccactcc
tgaggtctgaaggcagctcgctgtgtctgagcggtgcggagggaagtgccctgggagatttaaaatgtgagagtgggaggtgggaggttggtcctgtagg
cctcccatcccacgtgcctgcaacggagcccctagtgctactcagtcatgcccccgccagcaggggtcaggtcacttccatcctggggggttattatgactgttgtca
ttgttgttgccattttgctacccctaactggcagcggggtgctgcagagacctgatactgaccaggttcccctccggagctgacctgaacccccatgtcaccct
cgccccagcctgcagagggtggggtgactgcagagatccctttacccaaggccacagtcacatggttggaggagatggtgccaggcagaagccacccatc
caggatacaccctgccccagtgctggctctgacccgtccttgtctaagaggctgaccccagaagtgttcctgcgctgcagccagcctgaccccagagcctg
gacaccccctgcgccccactctgggggcgtaccaggaaccgtccaggcccagaggggcctcctgcttggcctcgaatggaagaaggcctcctattgtcct
cgtagaggaagcaacccaggccaaggataggccagggggatcgggaacgcgtgctggggccrggcccgggctggctggctggccctcctc
ctgtataaggccgagccgctgtctcagcccctccactcctgcagagctcagaagcgtgacccccagCTCGAGCTGCAGATGAAGGCTCT
CATTGTTCTGGGGCTTGTCCTCCTTTCTGTTACGGTCCAGGGCAAGGTCTTTGAAAGGTGTGAGTTG
GCCAGAACTCTGAAAAGATTGGGAATGGATGGCTACAGGGGAATCAGCCTAGCAAACTGTAAGTCT
ACTCTCCATAATTCCAGAGAATTAGCTACGTATGGAACAGACACTAGGAGAGAAGGAAGAAGAAG
AAGGGGCTTTGAGTGAATAGATGTTTTATTTCTTTGTGGGTTTGTATACTTACAATGGCTAAAAACA
TCAGTTTGGTTCTTTATAACCAGAGATACCCGATAAAGGAATACGG (SEQ ID NO.:42)

Figure 22

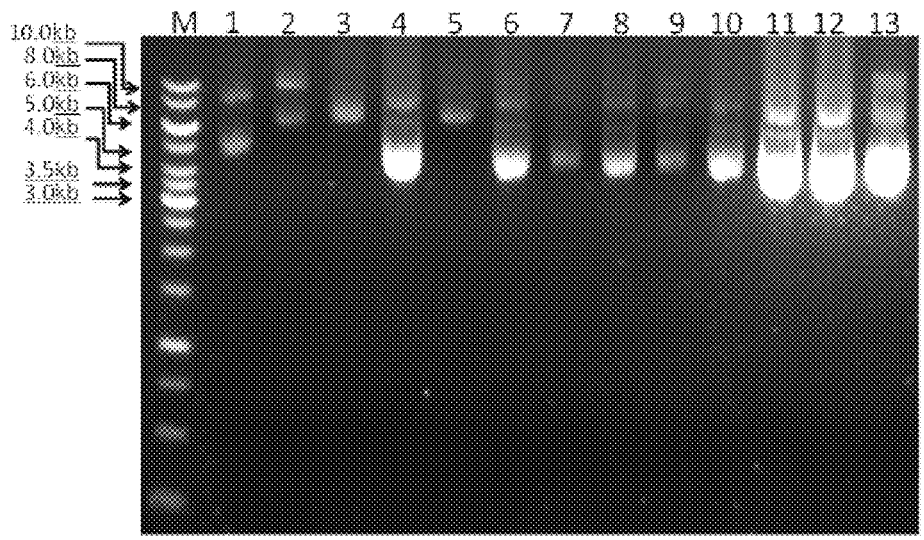

Figure 28

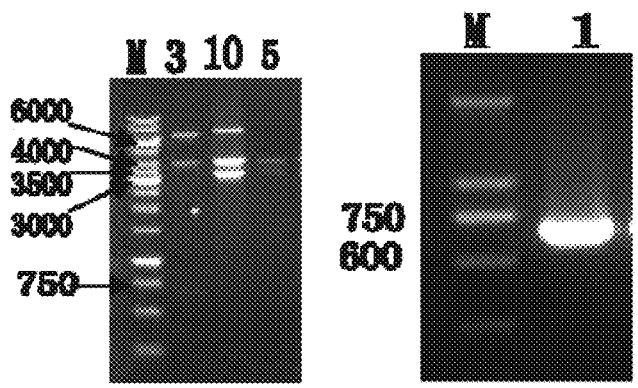

Figure 29

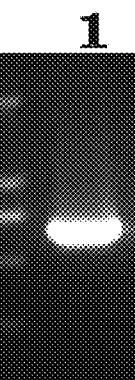

Figure 30

CACTTCTGGGGCGTACCAGGAACCGTCCAGGCCCAGAGGGGGCCTTCCTGCTTGGCCTCGAATGGAAGAAGGCCTCCTATTGTCCTCGT
AGAGGAAGCAACCCCAGGGCCCAAGGATAGGCCAGGGGGGATTCGGGGAACCGCGTGGCTGGGGGCCCGGCCCGGGCTGGCTGGCTGGC
CCTCCTCCTGTATAAGGCCCCGAGCCCGCTGTCTCAGCCCTCCACTCCCTGCAGAGCTCAGAAGCGTGACCCCAGCTCGAGtcgaggc
cgtcaccgtggagtgggtaaacttatttccttcttttctcttagtcggcttatccaggggtgtgttcgtcgagatgcacgta
agaatccatttttctattgttcagcttatttctattttctcagtagaatgaagtttagtaaactctgatctttaagagttatctt
ggcatttattttcaaaatggcatagttatttgtattgtgaagtcttacaggttatctattaataaattcaaacatcctaggtgaaa
aaaaaaaaggtcagaattgttagtgactgtaattttcttttgcgcactaggaagtgcaaagtaacttagagtgactgaaacttcac
agaatagggttgaagattgaattcataactatccaaagacttatttcattgcactatgtttattaaaatcacaaaacctgtgctgtt
gatctcataaatagaactgtattatattatttttattttagtctgtcttcttggttgctgttgatagacactaaagagtattagat
attatctaagtttga (SEQ ID NO.:43)

METHOD FOR POSITIONING AND INTEGRATING TRANSGENE AND USE THEREOF

TECHNICAL FIELD

The application relates to the field of biological technology and, in particular, to a method for positioning and integrating transgene and use thereof.

BACKGROUND

Methods for preparing transgenic animals are extremely important in the basic and applied researches. Up to present, scientists have developed many transgenic technologies to improve the targeting and integration efficiency in transgenic animals. However, in large animals, the transgenic integration efficiency and expression rate are not satisfactory.

The current universal transgenic method in the world is microinjection, which has high costs and low success rate. For a transgenic animal or a mammary gland bioreactor, the success rate can only reach about 3%. Microinjection results in random integration of an exogenous gene in chromosomes, and the transgenic expression is greatly influenced by the surrounding host genome. The random integration of an exogenous gene may cause the following questions. 1. The probability for integrating a transgene into inactive chromosomal sequences is higher than that for integrating into an active chromosomal region and most of transgenes are low expressed or not expressed at all because of the influence from the integration site. 2. When the transgene integrates into a high-frequency recombination site, it may cause genetic instability. 3. Random integration of an exogenous gene can often lead to mutation or altered expression of endogenous genes, thus effecting normal development and health of transgenic animals. 4. For a transgenic animal with integration in multiple sites, the isolation of integration sites in its offspring may lead to property change of transgenic expression and difficulty in breeding. 5. A significantly high or low copy number of integration may easily cause low or no transgenic expression.

The above questions are key barriers in the studies of gene function, creation of animal disease models, development of commercially valuable models and creation of transgenic breeding new materials. Developing a method for positioning and integrating transgene may overcome negative effects of high costs, low efficiency caused by the traditional technology, and promote industrial development of transgenic livestock. However, there is no method for controlling target gene to efficiently integrate into a specific site of genome. Therefore, there is an urgent need in the art to develop an efficient method for positioning and integrating transgene.

SUMMARY OF THE INVENTION

The object of the present invention is to provide a method for positioning and integrating transgene and use thereof.

In the first aspect of the present invention, it provides a mutant loxP element, and the loxP element comprises a sequence as shown in SEQ ID NO.: 30, or a sequence complete complementary to the sequence as shown in SEQ ID NO.: 30.

In the second aspect, a construct is provided, and the construct comprises from 5' to 3' the following elements:

(a) the mutant loxP element according to the first aspect of the present invention; (b) an expression cassette of an exogenous gene and/or an expression cassette of a selective gene for screening; (c) a wide-type loxP element having a sequence as shown in SEQ ID NO.: 28;

wherein element (a) and element (c) are interchangeable in position.

In another preferred embodiment, the screened marker is neomycin gene, or puromycin resistance genes.

In another preferred embodiment, the exogenous gene is selected from the group consisting of: lysozyme gene, salmon calcitonin gene, lactoferrin gene, and serum albumin gene.

In another preferred embodiment, element (a) and element (c) are placed in the same orientation. In another preferred embodiment, the element (a) and element (c) are placed in the opposite orientation.

In the third aspect, a vector is provided, and the vector contains a construct according to the second aspect of the present invention.

In the fourth aspect, a host cell is provided, and the host cell contains a construct according to the second aspect of the present invention, or a chromosome thereof is integrated with one or more constructs according to the second aspect of the present invention.

In another preferred embodiment, the host cell is human or non-human mammalian cell. In another preferred embodiment, the non-human mammal is selected from the group consisting of: goat, sheep, pig, cow, dog, and rabbit; and preferably, it is goat.

In another preferred embodiment, the host cell is a goat adult somatic cell, or a goat fetal somatic cell, or a goat embryonic stem cell.

In another preferred embodiment, the construct according to the second aspect of the present invention is introduced into the host cell by a method selected from the group consisting of: homologous recombination method, microinjection, electroporation, lipofection, calcium phosphate precipitation, virus infection method, or sperm-mediated gene transfer technique.

In the fifth aspect, it provides a method for preparing a transgenic animal, which comprises the following steps:

(i) in the presence of Cre recombinase, a cell in the fourth aspect of the present invention is transformed by a vector according to the third aspect of the present invention; and (ii) the transformed cell is regenerated into an animal, thereby obtaining a transgenic animal.

In another preferred embodiment, step (i) comprises steps of: (i-1) the cell in the fourth aspect of the present invention is co-transformed by a Cre enzyme expression vector and the vector according to the third aspect of the present invention; or (i-2) by using a TAT-Cre recombinant protein having a cell-penetrating activity, a chromosome of the cell in the fourth aspect of the present invention is genetically integrated with the vector according to the third aspect of the present invention.

In the sixth aspect, it provides a transgenic non-human mammal animal produced by the method according to the fifth aspect of the present invention.

In the seventh aspect, a method for producing a heterologous protein, which comprises the steps of: (i) feeding the transgenic non-human mammal animal (female) according to the sixth aspect of the present invention, thereby obtaining milk containing heterologous protein; and (ii) optionally, isolating the heterologous protein from the milk.

In another preferred embodiment, the heterologous protein is human protein.

In another preferred embodiment, the heterologous protein includes (but not limited to): lysozyme, salmon calcitonin, lactoferrin, serum albumin, or a combination thereof.

In the eighth aspect, it provides a milk product from non-human mammal animal, which comprises a high concentration of the heterologous protein.

In another preferred embodiment, in the milk without concentrating treatment, the content of the heterologous protein is 0.8-3 g/L. Preferably, the milk contains two or more heterologous proteins, and the content of each heterologous protein is 0.8-3 g/L.

It should be understood that, within the scope of the present invention, the technical features specifically described above and below (such as the Examples) can be combined with each other, thereby constituting a new or preferred technical solution which needs not be described one by one.

DESCRIPTION OF DRAWINGS

The drawings below are intended to illustrate the invention, but not to limit the scope of the present invention defined by the claims.

FIG. 19 shows the 5' end sequencing analysis result of a site-directed integrated clone of salmon calcitonin.

FIG. 20 shows the 3' end sequencing analysis result of a site-directed integrated clone of salmon calcitonin.

FIG. 21 shows the 5' end recombinant theoretical sequence of a site-directed integrated clone of salmon calcitonin (SEQ ID NO.:41).

FIG. 22 shows the 3' end recombinant theoretical sequence of a site-directed integrated clone of salmon calcitonin (SEQ ID NO.:42).

FIG. 28 shows electrophoretogram of plasmid pTM-hSA2. M is 1 kb DNA ladder; 1-12 are the electrophoretograms of the extracted plasmids, wherein, 3, 5 are positive plasmids; 13 is an electrophoretogram of the plasmid pTM-sCT2.

FIG. 29 shows an identification electrophoretogram of plasmid pTM-hSA2 in enzyme digestion. M is 1 kb DNA ladder; 3 is an electrophoretogram of the reverse insertion of hsA expression cassette into plasmid pTM-sCT2 framework; 5 is an electrophoretogram of the forward insertion of hsA expression cassette into plasmid pTM-sCT2 framework; and 10 is the negative control.

FIG. 30 shows an orientation identification pattern of plasmid pTM-hSA2. M is 1 kb DNA ladder; 1 is amplification electrophoretogram of plasmid pTM-hSA2 using primers for orientation identification.

FIG. 31 shows partial theoretical sequence of plasmid pTM-hSA2 (SEQ ID NO.:43).

FIG. 38 shows the 3' end recombinant theoretical sequence of a site-directed recombinant clone of human serum albumin (SEQ ID NO.:45).

FIG. 39 shows the 5' end sequencing results of a site-directed integrated clone of human serum albumin.

FIG. 43 shows sequence of human lactoferrin mini gene (SEQ ID NO.: 32). The underlined sequence is XhoI enzymatic digestion site for constructing the plasmid; the sequence shown in lowercase letters is the 15th intron sequence of genomic sequence of human lactoferrin; the sequence shown in capital letters is the cDNA sequence of human lactoferrin.

DETAILED DESCRIPTION OF INVENTION

Figure 1:
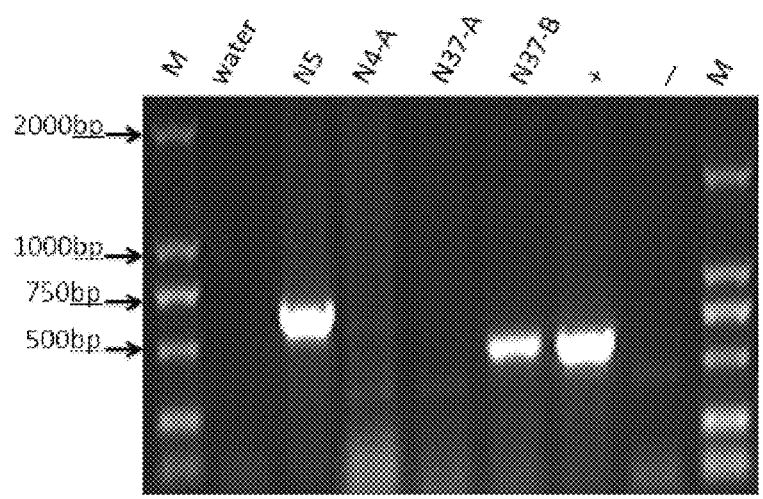
FIG. 1 shows the sex identification results of the goat fetal fibroblast. M is DL2000 Marker, and the bands from the bottom to the top are respectively 100, 250, 500, 750, 1000, and 2000 bp; N5, N4-A, N37-A and N37-B are all isolated from the fetus; "−" represents negative goat control; "+" represents positive goat control; water represents PCR system control.

After extensive and intensive researches, the inventors of the invention have unexpectedly found that when the reverse repeated sequence "ATAAC" in wide-type loxp site is mutated into "CACCT", the integration specificity and integration efficiency are greatly improved in cre-loxp integration system. In particular, when the mutation is introduced into the reverse repeated sequence at one side of the loxp site, and a plasmid having same mutant loxp site in the other side of the reverse repeated sequence is co-introduced, then an exogenous gene will be inserted in the presence of the Cre enzyme and a structure with two ends is formed, wherein one end is the wide-type loxp site and the other end has a bilateral mutant loxp site structure. Because the bilateral mutant loxp site is not a good substrate for Cre enzyme, the deleting reaction is prevented and the efficiency for forming stable integration is improved. Based on this, a highly efficient genomic site-directed strategy can be achieved. Based on the above findings, the present invention is completed.

Definition

Cre-LoxP System

The full length of the coding sequence of Cre recombinase is 1029 bp (EMBL Database Accession number: X03453) and encodes a protein of 38 kDa. Cre recombinase is a kind of monomeric protein, consisting of 343 amino acids, and belongs to μInt enzymatic supergene family. It not only has catalytic activity, but also recognizes the specific DNA sequence, i.e. loxP site (which is similar to restriction enzyme), thus deleting or recombining the sequence within the loxP sites.

The sequence of loxP (locus of X-over P1) is derived from the P1 bacteriophage, consisting of two 13 bp reverse repeated sequences and the 8 bp spacer region sequence located therebetween. The 8 bp spacer region sequence also determines the direction of loxP. Cre enzyme will covalently bind DNA during the exchanging process of catalyzed DNA strands, and the 13 bp reverse repeated sequences are the binding domain of Cre enzyme.

The sequence of wide-type loxP site is as follows:
5'-ATAACTTCGTATA-ATGTATGC-TATACGAAGTTAT-3' (SEQ ID NO.:28), and its complementary sequence is 3'-TATT-GAAGCATAT-TACATACG-ATATGCTTCAATA-5'(SEQ ID NO.:29).

As used herein, the term "loxP element" refers to two cis repeat sites that can be recognized by Cre recombinant protein. A mutant loxP element is provided in the present invention, the sequence of which is as follows: CAC-CTTTCGTATAATGTATGC TATACGAAGTTAT (SEQ ID NO.: 30).

As used herein, the term "Cre enzyme" refers to a protease that can mediate the specific recombination between 2 loxP sites, so that the nucleotide sequence between the loxP sites is deleted or recombined.

As used herein, "exogenous gene" refers to an exogenous DNA molecular having a periodic function. There is no special limitation for the exogenous gene useful in the present invention. It includes all kinds of exogenous gene common used in the transgenic animal field. Representative examples include (but are not limited to): lysozyme gene, salmon calcitonin gene, lactoferrin gene, or serum albumin gene, etc.

As used herein, "selective gene for screening" refers to a gene used to screen transgenic cells or transgenic animals during the transgenic process. There is no special limitation for selective gene for screening useful in the present invention. It includes all kinds of selective gene for screening that are common used in the transgenic field. The representative examples include (but are not limited to): neomycin gene, or puromycin resistance gene.

A construct is also provided in the present invention, which comprises from 5' to 3' the following elements:
(a) the mutant loxP element according to the present invention;
(b) an expression cassette of an exogenous gene; and/or an expression cassette of selective gene for screening;
(c) non-mutating (wide-type) loxP element as shown in SEQ ID NO.: 28;
wherein, element (a) and element (c) are interchangeable in position.

In a preferred embodiment, element (a) and element (c) are in the same or opposite orientation.

As used herein, the term "expression cassette" refers to a polynucleotide sequence containing a gene to be expressed and the sequence components for expressing the element of interest. For example, in the present invention, the term "expression cassette of selective gene for screening" refers to a polynucleotide sequence containing a sequence encoding the selective gene for screening and sequence components for expressing the element of interest. Moreover, the expression cassette of selective gene for screening may further include or not include other sequences, which includes (but are not limited to): enhancer, signal peptide sequence for secretion, etc.

In the present invention, the promoter suitable for expression cassette of exogenous gene and selective gene for screening can be any common promoter, either constitutive promoter or inducible promoter. Preferably, the promoter is a strong constitutive promoter, such as bovine β-lactoglobulin promoter and other promoters suitable for eukaryotic expression.

As used herein, "operably linked to" or "operably linked" refers to a situation in which some parts of a linear DNA sequence can affect the activity of other parts in the same linear DNA sequence. For example, if a signal peptide DNA is expressed as a precursor and involves in the secretion of polypeptide, then the signal peptide (secretory leader sequence) DNA is operably linked to polypeptide DNA; if a promoter controls transcription of a sequence, then it is operably linked to the encoding sequence; and if a ribosome binding site is positioned in a position where it can be translated, then it is operably linked to the encoding sequence. Generally, "operably linked to" means "neighboring", and, for secretory leader sequence, it means "neighboring" in reading frame.

All kinds of elements used in the construct according to the present invention are known in the art, so that the skilled in the art can use the common method (for example, the method of PCR, artificial chemical synthesis method, enzyme digestion method) to obtain the corresponding elements. Then the corresponding elements are connected together by any known technology of DNA ligation to form the construct of the present invention.

The construct according to the present invention is inserted into an exogenous vector (especially a vector suitable for operation in transgenic animals) to form the vector of the present invention.

A host cell is co-transformed by the vector of the present invention and the Cre enzyme expression vector. Alternatively, a chromosome of host cell is integrated by the vector of the present invention under the mediation by TAT-Cre recombinant protein having a cell-penetrating activity.

A method for site-directed integrating exogenous genes is also provided in the present invention, which comprises the steps of: in the presence of Cre enzyme, a cell of the invention is transformed by the vector of the present invention; and the transformed cell is regenerated into an animal, thereby obtaining a transgenic animal.

In a preferred embodiment of the present invention, it comprises the steps of:
(1) utilizing a gene-introducing method, a mutant loxp sequence is integrated into a specific position in a genome of livestock, thereby obtaining a cell having a loxp site-directed integration; (2) a gene framework to be introduced is placed between multiple loxp sites with same orientation, thereby forming a transgenic vector; (3) utilizing a gene-introducing method, the transgenic vector is introduced into the cell having loxp site-directed integration, and the gene framework is integrated at the loxp sites in the cell having loxp site-directed integration under the mediation by Cre enzyme, thereby obtaining a transgenic cell having a site-directed integration; and (4) utilizing a modern biological technology, an alive transgenic site-directed integrated animal is prepared by using the transgenic site-directed integrated cell.

The Major Advantages of the Present Invention Include:
(1) An exogenous gene can be high-efficiently integrated into a specific position in the livestock genome by the method of the present invention, thus avoiding random integration of the exogenous gene which may cause the integration site unclear and disturb expression of transgene.
(2) The plasmid containing an exogenous gene is directly transfected into cells by the method of the present invention, while without using enzyme digestion, gel electrophoresis, recovery and purification or other complex treatments, so that it extremely improves operability of plasmid construction, and saves human resources, material resources, and financial resources.
(3) In the transgenic site-directed integrated cells obtained by the method of the present invention, the location of the gene integration is clear, and the detection of gene integration is simple, thus avoiding the complex detection of traditional cell having transgenic integration and the excessive passages during the detection, thus making the genetically modified cells more suitable for cloning somatic cell.

(4) The method of the present invention can significantly simplify identification step during the safety evaluation and industrialization process of transgenic animals, it is of high-efficiency and good consistency. There is no significant influence from the transgenic fragment size on the efficiency of site-directed integration, and it is easy to be used in large scale.

(5) The method of the present invention can be used to conduct reversible treatment of integration and deletion of transgene, which is not only suitable for studying gene function and interaction, but also suitable for eliminating and deleting any harmful transgenes.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecular Cloning: A Laboratory Manual, New York: Cold Spring Harbor Laboratory Press, 1989, or as instructed by the manufacturers, unless otherwise specified.

EXAMPLE 1

Preparation of Cell Line Having Loxp Site-directed Integration

1. Isolation of Human Lysozyme Transgenic Goat Fetal Fibroblast

The commercial available female goat and the male goat containing the wide-type Loxp element (the male goat was disclosed in the patent ZL200510110772.1) were bred After 32-40 days, the fetus was taken out by using surgical method, and then transferred to a bechtop, washed twice with 1% PBS buffer containing two antibiotics (penicillin 100 U/ml, and streptomycin 0.1 mg/ml). The head, limbs and visceral were removed, the remaining tissue was soaked in the 75% ethanol for 30 s; then the fetal tissue was washed three to five times with PBS (without two antibiotics), cut into 1 mm³ size of tissue block. The tissue was evenly tiled on a 100 mm size of cellular petri dish, stood still in GMEM medium supplemented with 10% PBS, penicillin-streptomycin and non-essential amino acids (commercially available from Invitrogen, USA) at 37° C., 5% $CO_2$ incubator for 4 h. On day 2, GMEM medium was added around the tissue block and to immerse the tissue. Observation was conducted every 2-3 days and the medium was changed. Primary cells were cultured until 80% confluence of cell, and the cells were digested and collected, subcultured, countered, and cryopreserved in liquid nitrogen.

2. Identification of Human Lysozyme Transgenic Goat Fetal Fibroblast 4 fetuses were obtained, the situation of the fetal goat was shown as followed: N5 was a goat fetus of 32 days; N4-A was fetus of 37 days; N37-A was fetus of 37 days; N37-B was fetus of 37 days.

A pair of primers were designed according to the sequence of Y chromosome of goat:

SRY16f
(5'-caatcgtatgcttctgctatgttc-3' SEQ ID NO.: 1);

SRY654r
(5'-caatgttaccctatcgtggcc-3' SEQ ID NO.: 2).

A specific sequence of 638 bp on Y chromosome was specifically amplified. Based on that the sequence, the fetal sex identification was performed. If the specific sequence of 638 bp could be amplified from the sample, the sample was from male goat; Otherwise, it was from male goat.

Results (FIG. 1) showed that N5, N37-B were male goats, N4-A and N37-A were female goats.

A pair of primers were designed according to the sequence of the human lysozyme genome:

Lyz983
(5'-tacatttgaggacctggcagagc-3' SEQ ID NO.: 3);

Lyz1412
(5'-tcctaccactttgggaggctga-3' SEQ ID NO.: 4).

A specific sequence of the human lysozyme genomic fragment of 429 bp was amplified, and the identification of integration was performed. If the specific sequence of 429 bp could be amplified from the sample, the sample was from integrated fetus.

Figure 2:
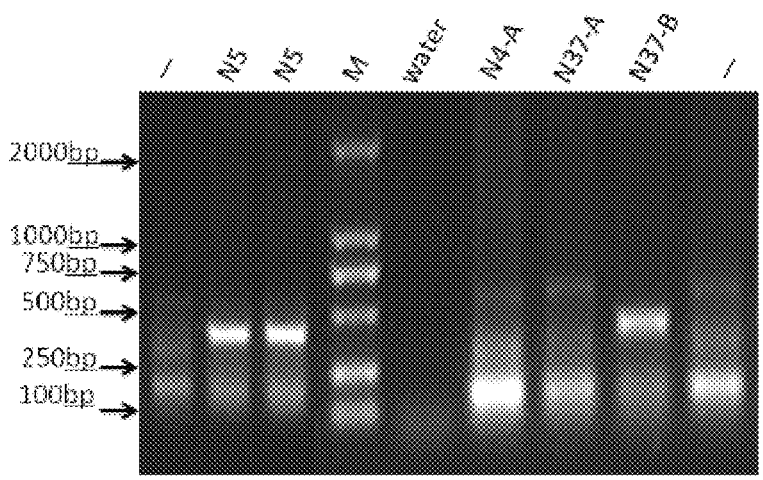
FIG. 2 shows identification results of the transgenic integration. M is DL2000 Marker, and the bands from the bottom to the top are respectively 100, 250, 500, 750, 1000, and 2000 bp; N5, N4-A, N37-A and N37-B are all isolated from the fetus; "−" represents negative goat control; "+" represents positive goat control; water represents PCR system control.

Results (FIG. 2) showed that N5 and N37-B were from integrated positive fetus.

EXAMPLE 2

Expression and Purification of TAT-Cre Enzyme

Expression plasmid pET 28.2 TAT-Cre containing TAT-Cre recombinase (The vector can be freely obtained from Howard Hughes Medical Institute. The information of structure, multiple cloning site (MCS), intact nucleotide sequence of the vector is from http://cmm ucsd.edu/Lab Pages/dowdy/Vectors/vector seq/pET28.2bTATCRE.txt) was selected. The bacterial colony having TAT-Cre recombinant expression plasmid was seeded in 20 ml LB medium containing kanamycin, and shaked overnight at 37° C. The overnight germ solution containing target plasmid was seeded according to 1:100 into 2 L kana LB medium, shaked for 3 h at 37° C. IPTG was added in a final concentration of 1 mmol/L to induce expression and it was shaked for 3 h at 37° C. After centrifugation at 3000 g for 10 min, the bacterial precipitate was obtained and resuspended in 100 ml pre-cooling PBS. After centrifugation at 5000 g for 10 min, the bacterial precipitate was obtained and this operation was repeated three times. The bacteria were stored in −80° C. for ready to use.

The bacteria containing target protein were resuspended in pre-cooling bacterial protein lysis solution, placed on the ice, and ultrasonically treated (intensity was 10) for 10 s. Then the mixture was placed on ice for 30 s to 1 min, and the operation was repeated several times until the bacteria were totally lysed. After centrifugation at 15000 g for 30 min, the supernatant was obtained, placed on ice. SP Sepharose™ column was balanced using 30% SB buffer ($Na_2HPO_4$ 10 mmol/L, glycerol 2.5%, β-mercaptoethanol 10 mmol/L, NaCl 1 mol/L, pH7.4) with a rate of 4 ml/min for 30 min. The supernatant from lysed bacteria was taken, filtered with 0.22 micrometer filter and loaded. The loading velocity was 4 ml/min. After loading, the column was washed using 30% SB buffer with a rate of 4 ml/min until the ultraviolet absorption value was stable and with no dropping. Gradient elution was conducted using 30% to 100% SB buffer (2 ml/min), and the total elute volume was 100 ml. All eluents were collected by automatic accumulator. Elution was continued using 100% SB buffer until the ultraviolet absorption value dropped to below 100 mAU.

The eluents above 250 mAU were combined, thus obtaining protein TAT-Cre recombinase.

The eluents were carefully mixed with two volumes of SA buffer (Na$_2$HPO$_4$ 10 mmol/L, glycerol 2.5%, β-mercaptoethanol, 10 mmol/L, pH7.4) on ice. After a small amount of precipitate formed, the mixture was filtered with 0.22 um filter, and the filtrate was placed on ice for use. The source 15 s column was balanced with 30% SB buffer for 15 s (4 ml/min, 30 min). The resulting supernatant after filtration was loaded with a loading rate of 4 ml/min. The column was eluted using 30% to 100% SB buffer until the peak was present. All the eluents above 250 mAU were collected, in which the target protein was contained. The target protein was loaded on HiPrep™ 26/10 Desalting column, eluted in buffer replacement (10 ml/min), and the eluted peak protein solution was collected.

After the peak protein solution was put into a millipore MWCO 30000 ultrafiltration tube, it was centrifuged at 3000 g for 30 min. More than about ¼ of the original volume of the protein solution was remained in the tube. The protein solution was sucked out and preserved at −80° C. Because each freeze-thawing operation had a certain influence on the concentration, the quantitative concentration of TAT-Cre recombinase was determined by DC before use.

Figure 3:
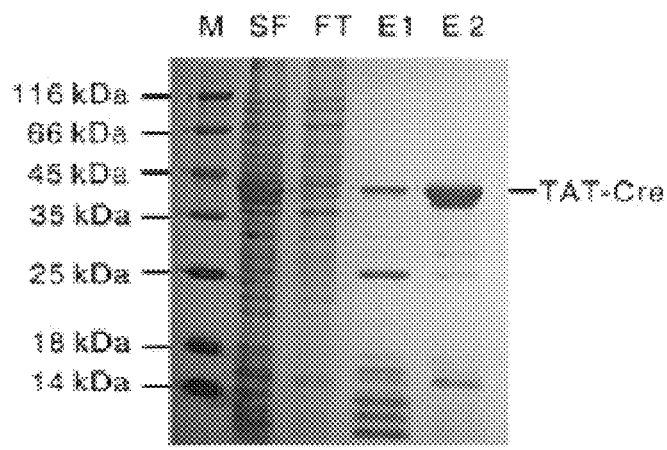
FIG. 3 shows the identification results of the TAT-Cre recombinant protein. M is marker, SF is supernatant after TAT-Cre bacteria ultrasonication, FT is flow through liquid of SP-Sepharose™ column, E1 is eluant of SP Sepharose™ column, and E2 is eluant of source 15 s column.

FIG. 3 showed the SDS-PAGE electrophoresis results of TAT-Cre recombinase. M was marker, SF was supernatant after ultrasonication treatment of TAT-Cre bacteria, FT was liquid flow of SP-Sepharose™ column, and E2 was elute from source 15 s column. The results showed that the TAT-Cre recombinase was successfully purified.

EXAMPLE 3

Introduction and Identification of Mutant Loxp Site

A complete sequence (as shown in SEQ ID NO.:31) was fully synthesized, wherein one side was a mutant Loxp site and the other side was a wide-type Loxp site in the same orientation; and in the middle were the expression frameworks of selective genes for screening, neo and TK. Then the sequence was cloned into SalI site of a commercial available vector pGEM-7Z, and the recombinant plasmid was named pGEM-2loxp'. Utilizing a loxp recombinant method mediated by TAT-Cre in Example 2, the element was then introduced into human lysozyme transgenic goat fetal fibroblasts so as to replace a selective marker gene which existed between the wide-type Loxp sites having same orientation. For the researches on transgenic element site-directed integration as described below, the human lysozyme transgenic goat fetal fibroblasts with mutant loxp site were used.

EXAMPLE 4

Construction of Salmon Calcitonin Site-directed Integration Plasmid pTM-sCT2

1. Overall Scheme of Vector Construction

Figures 4, 5:
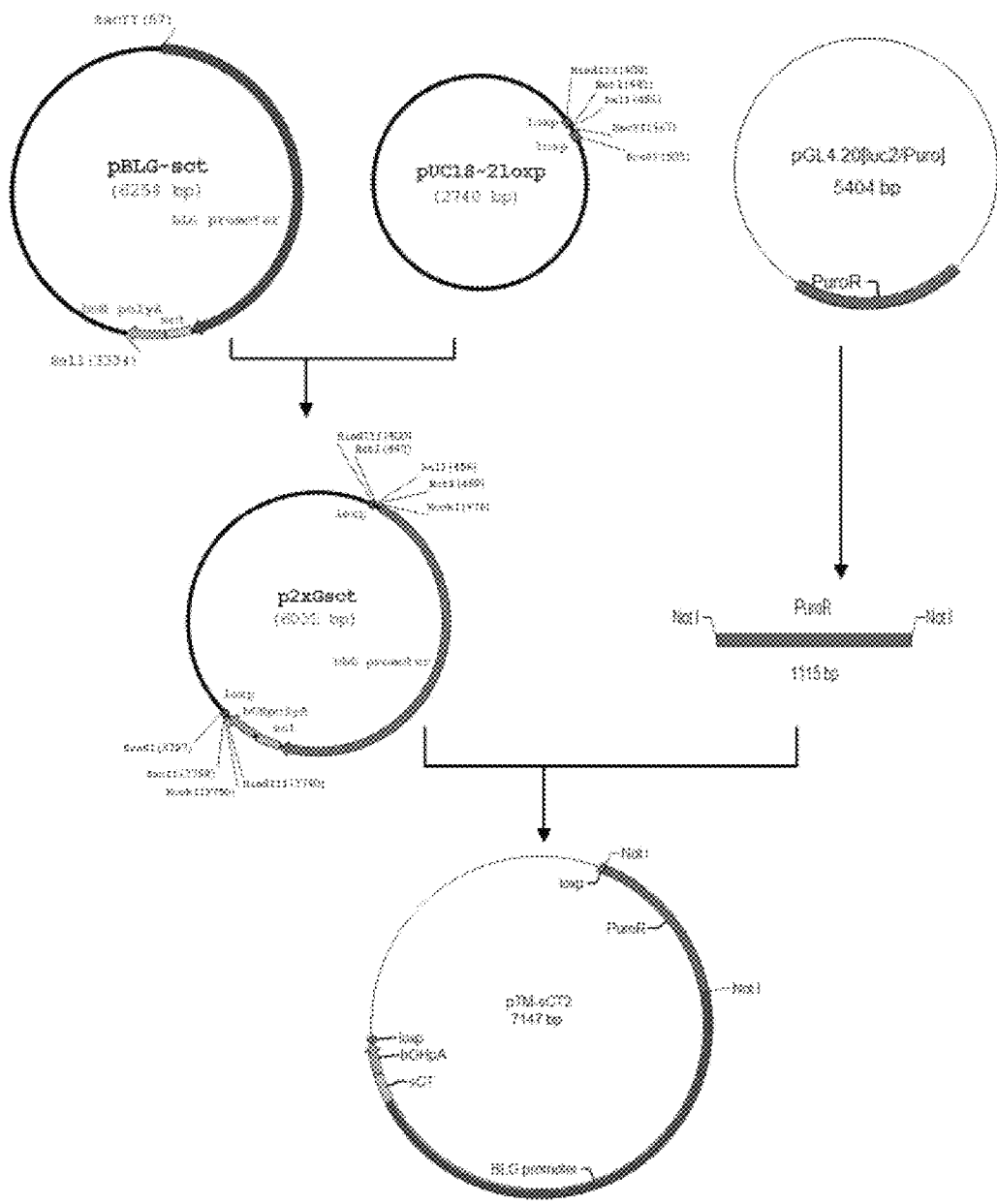
FIG. 4 shows a schematic diagram of construction of salmon calcitonin site-directed integration plasmid pTM-sCT2.
FIG. 5 shows the artificial synthesized double loxP gene sequence (SEQ ID NO.: 39).

According to the diagram in FIG. 4, a mammary breast-specific expression vector pTM-sCT2 for salmon calcitonin was constructed, which had two loxp sequences. The preparation method of pbLGpA was disclosed in the Chinese patent ZL200510110772.1. This plasmid pbLGpA contained a breast-specific expression regulatory framework which contained a bovine β-lactoglobulin promoter and a bovine growth hormone polyA sequence.

2. Construction of a Vector with Double Loxp Sites

The sequence with double loxp sites was fully synthesized and the sequence was shown in FIG. 5. The sequence was cloned into a commercial available pUC18 vector, and the resultant plasmid was named pUC18-2loxp.

Between the 2 loxp sites was introduced a multiclonal site consisting of SacI, SalI and NotI so as to facilitate the subsequent gene cloning.

3. Construction of the Salmon Calcitonin Breast-specific Expression Vector

Figures 6, 7:
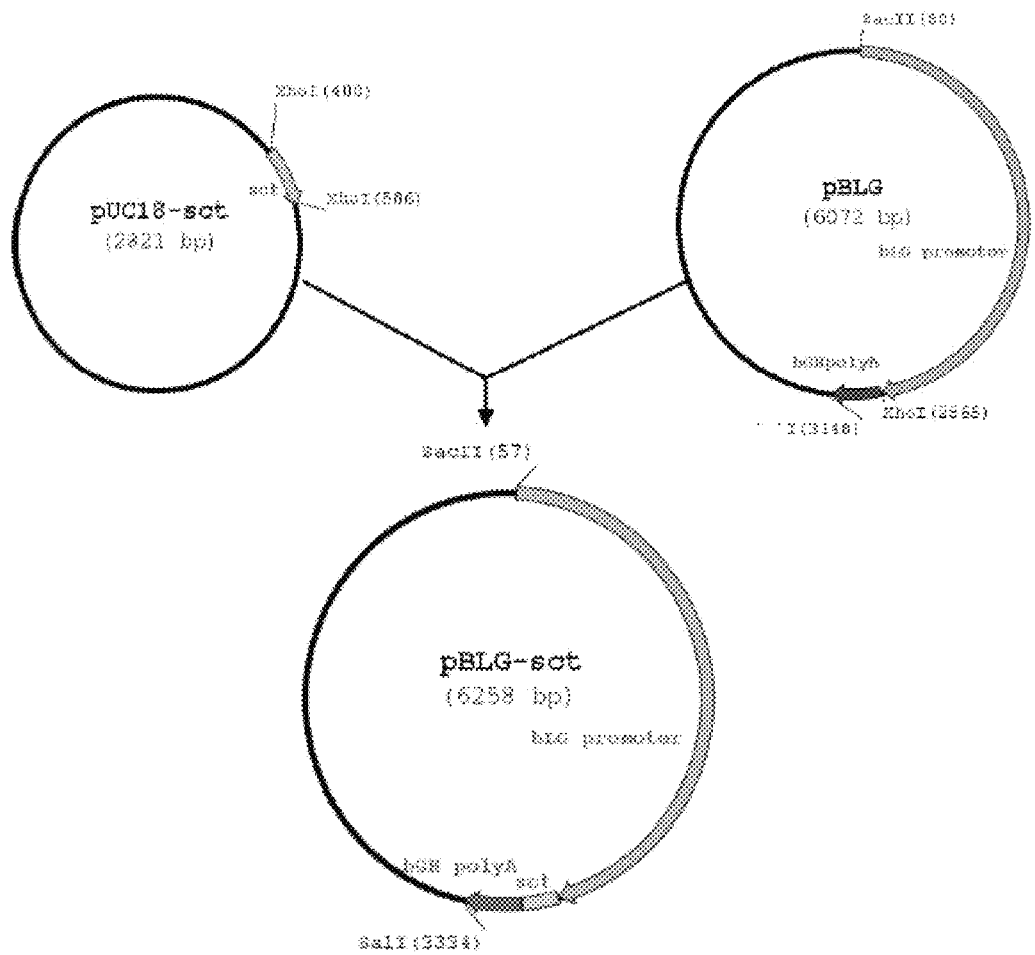
FIG. 6 shows a schematic diagram of construction of pBLG-sct plasmid.
FIG. 7 shows the completely artificial synthesized salmon calcitonin sequence (SEQ ID NO.:40).

According to the diagram in FIG. 6, the salmon calcitonin breast-specific expression vector pBLG-sCT was constructed. Plasmid pbLGpA contained a breast-specific expression regulatory framework including a bovine β-lactoglobulin promoter and a bovine growth hormone polyA sequence. FIG. 6 showed a schematic diagram for constructing plasmid pBLG-sct.

The encoding sequence of salmon calcitonin (sCT) was artificially synthesized by Shanghai Generay Biological Engineering Co. Ltd (FIG. 7). In order to secret salmon calcitonin into milk and to facilitate purification, three elements were added in front of the encoding framework of salmon calcitonin, which included a goat β-casein secretory peptide, 6His tag and enterokinase cleavage site, and was flanked by XhoI site. The sCT sequence was cloned into pUC18 vector, thereby forming plasmid pUC18-sCT. FIG. 7 showed the sequence of artificial synthetic salmon calcitonin.

4. Construction of sCT Breast-specific Expression Vector with Double Loxp Sites

Using plasmids pBLG-sct and pUC18-2loxp digested with SalI and SacII, the sCT expression cassette was inserted between double loxp sites, thereby obtaining a sCT breast-specific expression plasmid p2xGsct with double loxp sites.

5. Cloning of Puromycin Resistance Gene Expression Cassette

Based on the sequence of plasmid pGL4.20[luc2/Puro] (Commercially available from Promega Corporation, GenBank Accession Number: DQ1888 40), the following primers were designed and synthesized:

```
F-puro1183
(5'-ttgcggccgcgataaggatccg tttgcgta-3'
SEQ ID NO.: 5);

R-puro1183
(5'-ttgcggccgcatcggtcgacagcatctagt-3'
SEQ ID NO.: 6).
```

The puromycin resistance gene expression framework was amplified.

Figure 8:
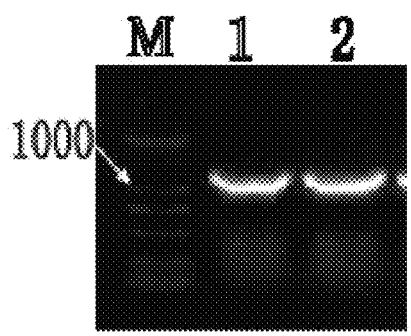
FIG. 8 shows an amplification electrophoretogram of a puro expression cassette. M is D2000 marker; 1 and 2 represent amplification electrophoretogram of the puro expression cassette.

After successfully detecting with 2% agarose gel electrophoresis, the gene expression fragment was purified, recovered and screened using TIANGEN DNA purification and recovery kit. The recovered band and vector pGM-T were linked and transformed into competent DH5α strain, thereby obtaining plasmid pMD-Puro (FIG. 8, wherein M is D2000 marker; the bands from the bottom to the top are respectively 100, 250, 500, 750, 1000, and 2000 bp; 1 and 2 are the electrophoretograms of amplification of puro expression framework).

Figure 9:
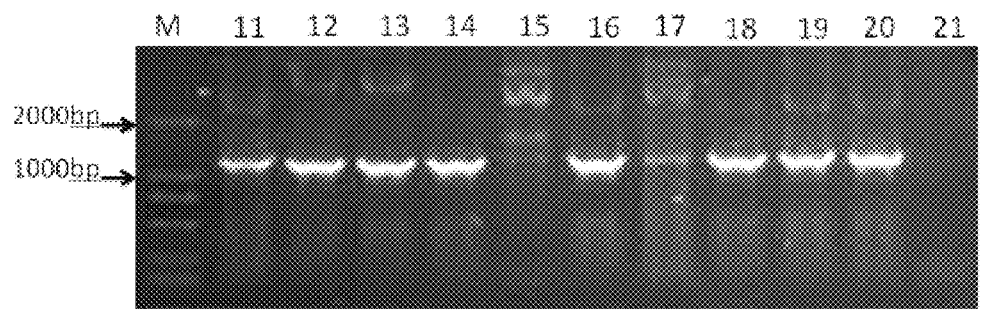
FIG. 9 shows PCR identification of plasmid pMD-Puro. M is D2000 marker; 11-20 represent the selected transformant clones; 11, 12, 13, 14, 16, 17, 18, 19, 20 are positive clones; and 21 is negative control.
Figure 10:
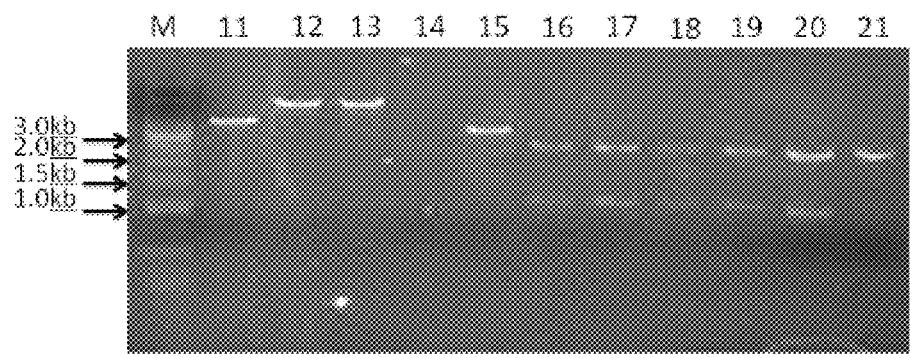
FIG. 10 shows electrophoretogram of plasmid pMD-Puro identification by Not I digestion. M is 1 kb marker; 11-20 represent the picked transformant clones, wherein 16, 17, 18, 19, 20 are positive clones.

The identification of pMD-Puro was conducted by using PCR method (FIG. 9, wherein M is D2000 marker; 11-20 represent the selected clones after transformation; 11, 12, 13, 14, 16, 17, 18, 19, 20 are positive clones; 21 represents a negative control, and the target band is 1183 bp) and enzyme digestion identification (FIG. 10, wherein M is 1 kb ladder;

11-20 represent selected clones after transformation; 16, 17, 18, 19, 20 are positive clones, the target band is 1183 bp) respectively.

The identification results showed that the plasmid was constructed correctly.

6. Construction of Salmon Calcitonin Site-directed Integration Plasmid.

The Puro expression cassette was obtained by NotI digestion of plasmid pMD-Puro, and then inserted into a linear p2xGsct digested with NotI, thereby obtaining salmon calcitonin site-directed integration plasmid pTM-sCT2.

Figure 11:
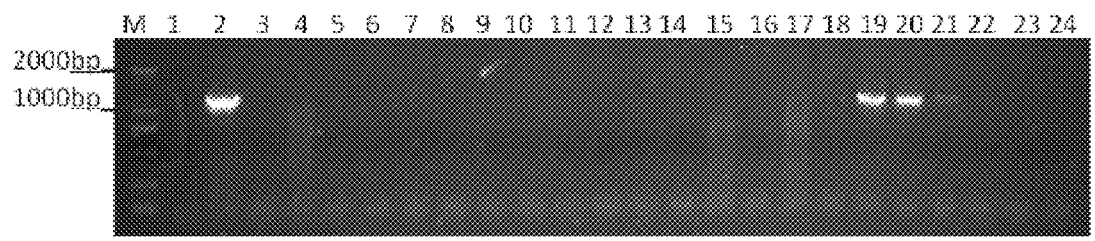
FIG. 11 shows PCR identification pattern of pTM-sCT2. M is D2000 marker; 1-23 represent the selected monoclones: 2, 19, 20 are positive clones; and 24 represents negative control.

The identification showed that there were 4 positive clones out of 23 colonies. The expected band of 1183 bp was obtained by PCR (FIG. 11, wherein M is D2000 marker; 1-23 represent selected monoclones and 2, 19, and 20 are positive clones; 24 represents a negative control).

Figure 12:
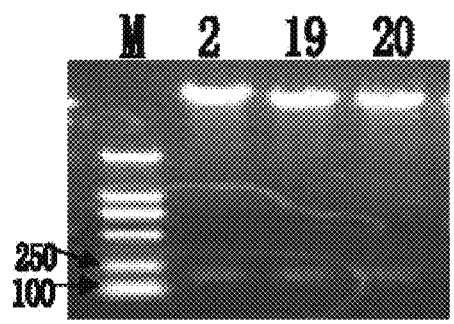
FIG. 12 shows electrophoretogram of plasmid pTM-sCT2 as identified by Not I digestion. M is D2000 marker; and 2, 19, 20 are positive clones.
Figure 13:
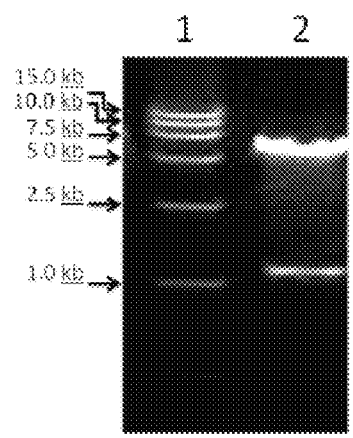
FIG. 13 shows an identification pattern of pTM-sCT2 as identified by enzyme digestion; wherein 1 is DL5000 DNA Marker, and 2 is the electrophoretogram of plasmid pTM-sCT2 digested with Not I enzyme.

The further identification showed that pTM-sCT2 could be digested by XhoI to produce a sCT fragment of 180 bp (FIG. 12, wherein M is D2000 marker; 2, 19, and 20 are positive clones). The Puro expression cassette of 1183 bp was obtained by Not I enzyme digestion (FIG. 13, wherein 1 is BM15000 DNA Marker II, and the bands from the top to the bottom are respectively 500, 1000, 1500, 3000, 5000, 7500, 10000, and 15000 bp; 2 shows electrophoretogram of plasmid pTM-sCT2 digested by NotI enzyme), indicating that the plasmid was successfully constructed.

EXAMPLE 5

Site-directed Integration Achieved by Co-transfection of pBS185 and pTM-sCT2

1. Preparation of Plasmids pTM-sCT2 and pBS185 pBS185 was commercially available from Addgene corporation.

Plasmid pTM-sCT2 was obtained in the Example 4.

Each plasmid was extracted in large amount by using EndoFree Plasmid Maxi Kit (Cat. No. 12362) of QIAGEN. The final concentration of plasmid pBS185 was 485 ng/µl, 500 µl totally, and the concentration of plasmid pTM-sCT2 was 1.9 ng/µl, 500 µl totally.

2. Co-transfection of pBS185 and pTM-sCT2 to BLG3 Cell

The human lysozyme transgenic goat fetal fibroblasts was recovered on the 60 mm cell petri dish, grown in the complete medium and passaged to a 24-well plate, 4×10⁵ cells/well, 500 µl of medium without double-antibiotics was added to each well. By the next day, cells were grown to 50-80% confluence, and could be used for transfection. Before transfection, the DNA-lipid complex was prepared according to the following method. The plasmids (pBS185 and pTM-sCT2 added in an amount ratio of 1:1) were prepared as Table 1, and were group numbered (according to 24-well plate coordinates), each tube of plasmid was diluted with 100 µl Opti-MEM® I serum-free medium (available from Invitrogen, USA), and well mixed. Before use, the PLUS reaction solution (available from Invitrogen, USA) was gently mixed, and into the diluted plasmid was added 1 µl of PLUS reaction solution, mixed gently, then stood still at the room temperature for 5 min. Lipofectamine™ LTX (available from Invitrogen, USA) was gently mixed. Into each of the tube above was added the reagent (the amount shown in Table 1), mixed well. Stood still at the room temperature for 30 min. To 24-well plate was dropwise added with 100 µl formulated above DNA-lipid complexes, the culture plate was gently slided back and forth, and well mixed. The treated cells above were incubated in a 37° C. incubator (5% $CO_2$ of volume fraction) for 6 h, then additional cultured on the complete medium, after the cells became adherent, they were washed three times in PBS, and OPTI-MEM was added to dilute TAT-Cre (2 µM of final concentration). After 3 hours of treatment, it was replaced with normal culture medium to additionally culture.

TABLE 1

| Group | | B | C | D | A |
|---|---|---|---|---|---|
| 1 | amount of plasmid/ng | 250:250 | 375:375 | 500:500 | 0 |
|   | amount of liposome/µl | 2 | 2 | 2 | 2 |
| 2 | amount of plasmid/ng | 250:250 | 375:375 | 500:500 | 0 |
|   | amount of liposome/µl | 3 | 3 | 3 | 3 |

The selection and identification of integrated clonal cell lines. After the above cells were additionally cultured for 24 h, the cells in each well were plated into a 100 mm cell petri dish, 16 totally. 0.08 µg/ml of Puromycin was used for pressure selection for 10 days, the monoclonal cells were transferred into 96-well cell culture plate by using a cloning ring, and the number of picked clones were shown in Table 2.

TABLE 2

| Group | The number of clones in Group A/clones | The number of clones in Group B/clones | The number of clones in Group C/clones | The number of clones in Group D/clones |
|---|---|---|---|---|
| 1 | 0 | 7 | 5 | 4 |
| 2 | 0 | 5 | 10 | 13 |

The cells were passaged into 48-well cell culture plate by normal culture method. The grown cells were digested as 2 parts, in which one part was used in the integration of identification, while the other part was further cultured for propagation and frozen preserved for somatic cell cloning.

3. Site-directed Recombinant Identification of sCT Transgenic Framework 3.1 Extraction of the Cellular Genome The cellular genome was extracted with cellular genome extraction kit (Product code: Dp302-02) from Tiangen Biotech (Beijing) Co., Ltd, and the concentration was adjusted to about 50 ng/µl.

3.2 Identification of Integrated Cellular Clones

According to the recombinant theoretical sequence, the detection primers shown in Table 3 were designed:

TABLE 3

| | Primers | Bp | Location |
|---|---|---|---|
| P1 (detection of 5'-end) | F: 5-CAAGCCACCTAACCTCACTG-3 SEQ ID NO.: 7 R: 5-TCGTAGAGGAAGCAACCC-3 SEQ ID NO.: 8 | 820 | genome of goat (5'-end) pbLGpA |

TABLE 3-continued

| | Primers | Bp | Location |
|---|---|---|---|
| P2 (detection of 3'-end) | F: 5-TTCTGACACTAGCGCCACC-3 SEQ ID NO.: 9 | 808 | Expression cassette of Puro |
| | R: 5-GCCAGCTCCCATTAGCTTG-3 SEQ ID NO.: 10 | | genome of goat (3'-end) |
| detection of Neo | F: 5-CTGCTATTGGGCGAAGTGC-3 SEQ ID NO.: 11 | 469 | neo gene |
| | R: 5-CGGCGATACCGTAAAGCAC-3 SEQ ID NO.: 12 | | neo gene |
| detection of Sct | F: 5-ACCTACTCAGACAATGCGATGC-3 SEQ ID NO.: 13 | 1100 | sct gene |
| | R: 5-CGGAGCCCTAGTGCTACTCA-3 SEQ ID NO.: 14 | | sct gene |
| detection of pBS185 | F: 5-TTACGGCGCTAAGGATGA-3 SEQ ID NO.: 15 | 357 | pBS185 gene |
| | R: 5-CTTTACAGTGACAATGACGGC-3 SEQ ID NO.: 16 | | pBS185 gene |

Figure 17:
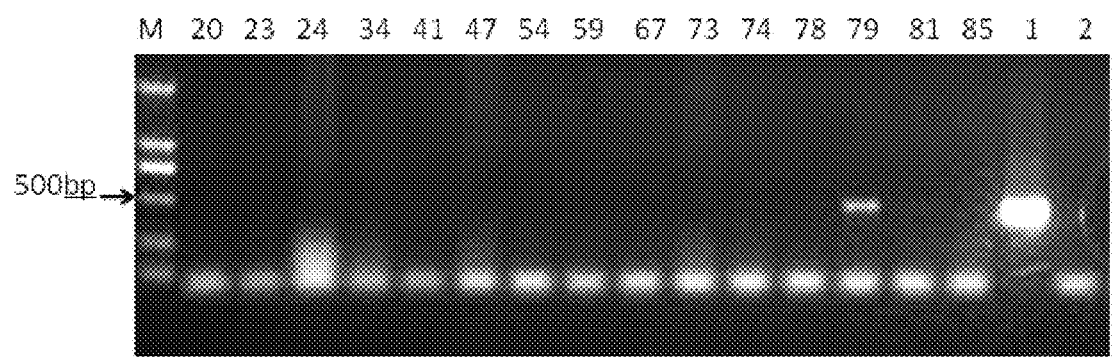
FIG. 17 shows detection electrophoretogram for screening neo gene. M is D2000; 20, 23, 24, 34, 41, 47, 54, 59, 67, 73, 74, 79, 81, 85 are detection electrophoretograms for screening neo as clone selection gene; 79 is positive gene neo, 1 is the positive control, and 2 is the negative control.
Figure 18:
FIG. 18 shows detection electrophoretogram of pBS185 gene. M is D2000; 23, 24, 34, 47, 59, 74, 78, 81, 85 are detection electrophoretograms for screening cloned gene pBS185, wherein 24, 34, 81 represent a positive gene and 0 represents a negative control.

The recombinant clonal genome extracted with the primer pairs above was detected respectively for 5'-end (FIGS. 14 and 19), 3'-end (FIGS. 15 and 20), functional gene (sct) (FIG. 16), selectable marker gene (Neo) (FIG. 17), and plasmid pBS185 gene (FIG. 18). The detection method was PCR (94° C. pre-denaturate for 5 min, 94° C. 30 s Tm 30 s, 72° C. 1 min (/3 min), 72° C. 7 min).

Figure 14:
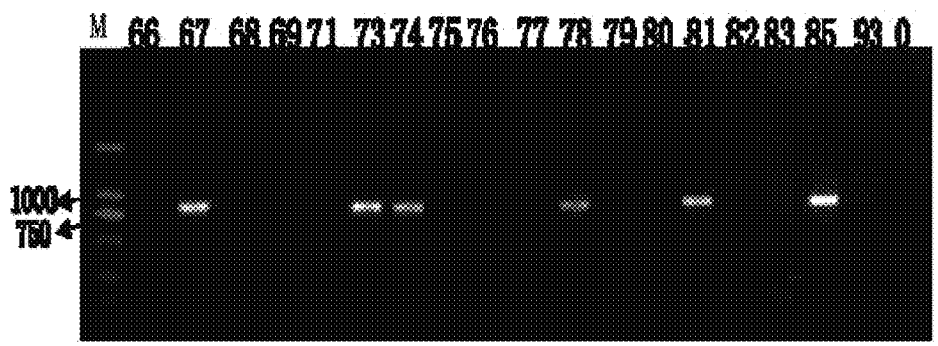
FIG. 14 shows detection electrophoretogram for screening 5' end clones. M is D2000; 66-69, 71, 73-85, 93 are all detection electrophoretograms for screening 5' end clones; 67, 73, 74, 78, 81, 85 are positive, and 0 is the negative control.

FIG. 14 shows 5'-end detection results of recombinant clones, wherein M is DL2000; 66-69, 71, 73-85, 93 are all the 5'-end detection results of clones; 67, 73, 74, 78, 81, 85 are positive; 0 is the negative control.

Figure 15:
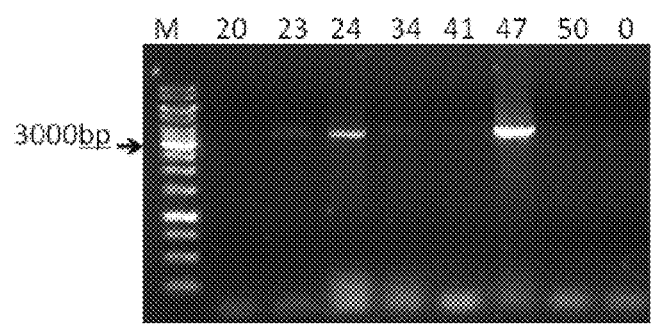
FIG. 15 shows detection electrophoretogram for screening 3' end clones. M is 1 kb DNA Marker; 20, 23, 24, 34, 41, 47, 50 are detection electrophoretograms for screening 3' end clones, and 0 is the negative control.

FIG. 15 shows 3'-end detection results of recombinant clones, wherein M is 1 kb DNA Marker; 20, 23, 24, 34, 41, 47, and 50 are 3'-end detection electrophoretograms of selected clones; 0 is the negative control.

Figure 16:
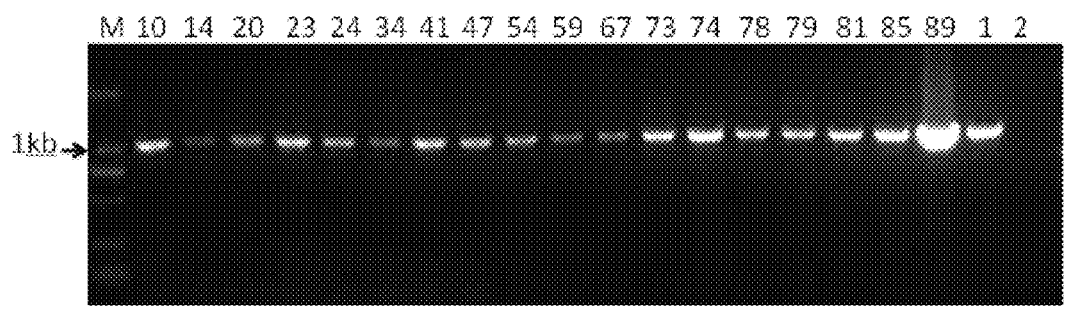
FIG. 16 shows detection electrophoretogram of the salmon calcitonin functional gene. M is D2000; 10, 14, 20, 23, 24, 34, 41, 47, 54, 59, 67, 73, 74, 79, 81, 85, 89 are detection electrophoretograms of the functional gene neo, 1 is the positive control, and 2 is the negative control.

FIG. 16 shows detection electrophoretogram of the salmon calcitonin functional gene; wherein M is DL2000; 10, 14, 20, 23, 24, 34, 41, 47, 54, 59, 67, 73, 74, 79, 81, 85, and 89 are detection electrophoretograms of the functional gene neo; 1 is the positive control; and 2 is the negative control.

FIG. 17 shows detection results of the selected gene neo; wherein M is DL2000; 20, 23, 24, 34, 41, 47, 54, 59, 67, 73, 74, 79, 81, and 85 are the detection electrophoretograms for screening neo as clone selection gene; 79 is positive gene neo; 1 is the positive control; and 2 is the negative control.

FIG. 18 shows detection electrophoretogram of pBS185 gene, wherein M is DL2000; 23, 24, 34, 47, 59, 74, 78, 81, and 85 are detection electrophoretograms for screening cloned gene pBS185; 24, 34, and 81 are positive for gene; and 0 represents a negative control.

FIG. 19 shows the 5' end sequencing analysis result of a site-directed integrated clone of salmon calcitonin.

FIG. 20 shows the 3' end sequencing analysis result of a site-directed integrated clone of salmon calcitonin.

The above results of detection and sequencing were coincident with the theoretical sequence (FIGS. 21 and 22).

Totally 44 calcitonin transgenic integration cell clones were detected, wherein 9 site-directed integration positive clones were obtained. In the 6 transfection conditions, the best site-directed integration efficiency was 40%(⅖), while the other site-directed integration efficiency were 20% (⅕), 2/10), 23.1%(3/13), and 25%(¼) respectively. 4 lines integrated with pBS185 were found, which could not be used in the preparation of clonal goat. Sequencing analysis of PCR products was performed for the screened representative positive clones, and it was found by the BLAST that the results were consistent with the theoretical sequence. The results above all showed that the site-directed recombination of exogenous functional genes into human lysozyme transgenic goat genome was successfully achieved.

EXAMPLE 6

Site-directed Integration Achieved by Plasmid pTM-sCT2 Mediated by TAT-Cre

1. Liposome Transfection

The method was the same to the pBS185 and pTM-sCT2 co-transfection method for achieving site-directed integration. The amount of the plasmid added was shown in Table 4.

TABLE 4

| | Groups | B | C | D | A |
|---|---|---|---|---|---|
| 1 | amount of plasmid/ng | 500 | 750 | 1000 | 0 |
| | amount of liposome/μl | 2 | 2 | 2 | 2 |
| 2 | amount of plasmid/ng | 500 | 750 | 1000 | 0 |
| | amount of liposome/μl | 3 | 3 | 3 | 3 |

The results showed that among the selected 49 clones, 2 of them were positive clonal cell lines. In the transfection conditions of 6, the recombinant efficiency were 20% (⅕), and 12.5% (⅛). The identification results were shown in FIGS. 13-17.

2. Electroporation Transfection

Plasmid pTM-sCT2 was quantified into a concentration of 1.9 μg/μl, and 7 μl was taken for further use.

The human lysozyme transgenic goat fetal fibroblasts were recovered on the 60 mm cell petri dish, and were passaged into the 100 mm cell petri dish after grown to confluence. The cell transfection was started when the cell density was about 80%. The number of the cells was counted after the cells were digested by trypsin, the cells were centrifuged at 1000 rpm for 5 min, and then resuspended in the electroporation buffer PBS, and the number of the cells was adjusted to 5×10⁶-1×10⁷ cells/mL. 500 µl cell suspension was taken, and 12 µg of circular plasmid pTM-sCT2 filtered by 0.22 um filter was added into the cell suspension, well mixed, added to a pre-cooled 4 mm electroporation cup, stood still on ice for 5 min and transferred to the electroporation device for electric shock in a 220V pulse voltage of and 950 µF capacitance. After electric shock, the cell suspension was put on ice for 10 min, and then transferred into the 100 mm culture plate with culture solution, cultured in 37° C., 5% $CO_2$. The cells were washed with PBS for 3 times after became adherent. The OPTI-MEM was added to dilute TAT-Cre (2 µM of final concentration). After treated for 3 h, it was replaced with the normal culture solution to further culture. After 24 h, the digested cells were transferred into 6-8 100 mm cellular culture plate, and puromycin (final concentration: 0.08 µg/ml) was used to pressure select for 7 days. The monoclonal cells were transferred into 96-well cellular culture plate by using a cloning ring, and were cultured by normal passage method. After growing to confluence in 48 wells, the cells were digested as 2 parts, in which one part was used in the integration of identification, while the other part was further cultured and frozen preserved for somatic cell cloning.

3. Site-directed Recombinant Identification of sCT Transgenic Framework

The genome of selected clonal cell lines was extracted and preserved in 4° C.

Figure 23:
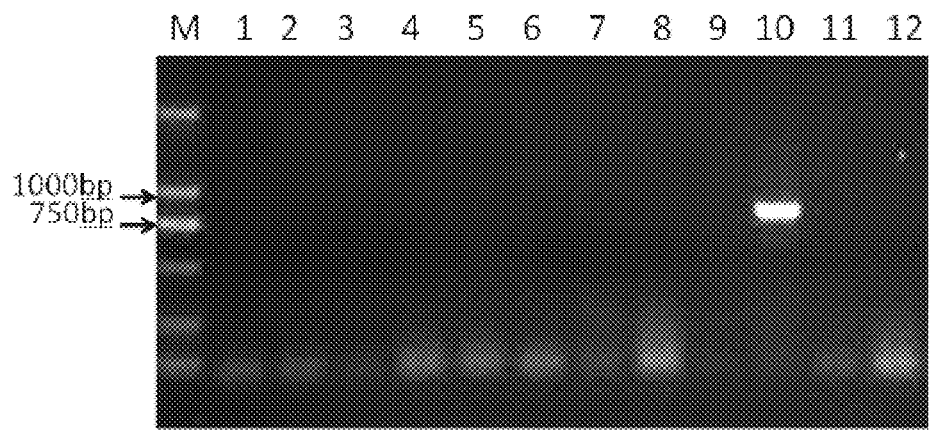
FIG. 23 shows the 5' end detection electrophoretogram for screening a clonal cell line. M is D2000 marker; 1-12 are the 5' end detection electrophoretogram of the selected clonal cell lines, and 10 is the positive clone.
Figure 24:
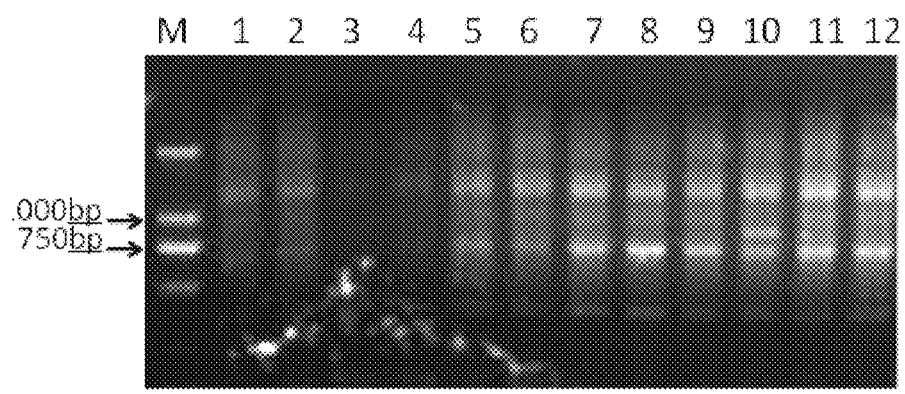
FIG. 24 shows the 3' end detection electrophoretogram for screening of a clonal cell line. M is D2000 marker; 1-12 are the 3' end detection electrophoretogram of the selected clonal cell lines, and 10 is the positive clone.
Figures 25, 26, 27:
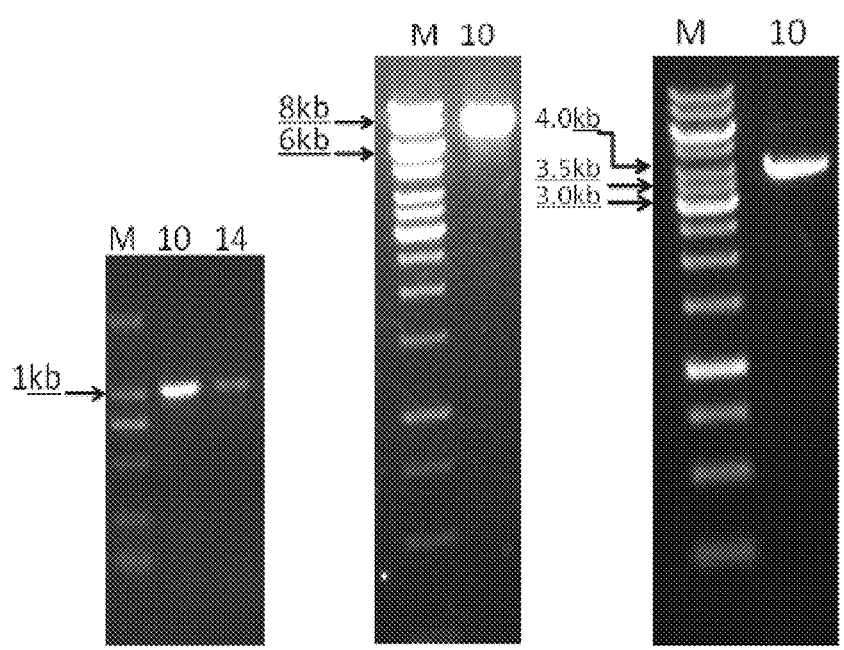
FIG. 25 shows detection electrophoretogram of functional gene. M is D2000 marker; 10 and 14 are detection electrophoretograms for screening clonal functional gene sct.
FIG. 26 shows the recovered pTM-sCT2 plasmid framework. M is 1 kb DNA ladder; 1 shows the recovered pTM-sCT2 plasmid framework.
FIG. 27 shows the recovered hsA expression framework. M is 1 kb DNA ladder; 1 shows the recovered hsA expression framework.

As shown in FIGS. 23, 24 and 25, the results indicated that in the 18 detected transfection clonal cell lines, 2 of them were positive clones, and the recombinant efficiency was 2/18=11.1%.

FIG. 23 shows a 5' end detection electrophoretogram of the selected clonal cell line; wherein M is DL2000 marker; 1-12 are the 5' end detection electrophoretogram of the selected clonal cell lines, and No. 10 is the positive clone.

FIG. 24 shows the 3' end detection electrophoretogram for screening of a clonal cell line; wherein M is DL2000 marker; 1-12 are the 3' end detection electrophoretogram of the selective clonal cell lines, and 10 is the positive clones.

FIG. 25 shows detection electrophoretogram of functional gene; wherein M is DL2000 marker, 10, and 14 are the detection electrophoretogram of the selected clonal functional gene sct.

EXAMPLE 7

Preparation of Mammary Breast-specific Expression Cassette of Human Serum Albumin Mini Gene According to the genomic sequence of human serum albumin, human serum albumin mini gene was fully synthesized, of which the full-length was 4015 bp, including partial sequences of exon1, intron1, exon2, intron2, exon3 and all cDNA encoding sequences (the complete sequence was shown in SEQ ID NO.:27). The sequence was then cloned into a commercial available pUC19 vector after synthesized, and the plasmid was named pUC19-miniHSA.

pUC19-miniHSA was digested by Xho I enzyme to obtain the human serum albumin mini gene. The product was then recovered and site-directed inserted into the XhoI site of plasmid pbLGpA. PCR identification was performed using a pair of orientation identifying primers HSAg-Fnew (GTGGGTAACCTTTATTTCC) and T7(TAATACGACT-CACTATAGGG) for 55 single colonies. Only NO.9 has amplified the 4394 bp target fragment. The NO.9 bacterial solution was sent for sequencing, and the NO.9 plasmid was sequenced and it was found to that it was a clone with correct insert-orientation. Thereby, the human serum albumin mini gene regulated by bovine lactoglobulin albumin to obtain mammary breast-specific expression cassette was obtained, and the plasmid was named pBLG-minihSA.

Figure 42:
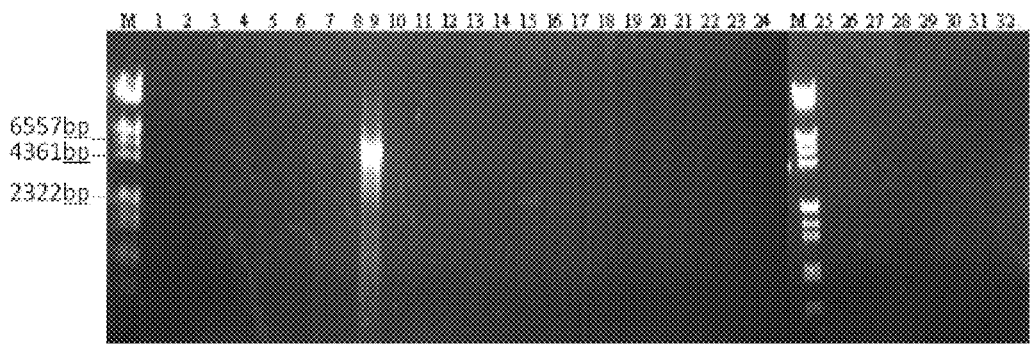
FIG. 42 shows the identification result of a mammary breast-specific expression vector for human serum albumin.

FIG. 42 shows the identification results of mammary breast-specific expression vector of human serum albumin, wherein M is λ/HindIII DNA Marker; each band is respectively 23130, 9416, 6557, 4361, 2322, 2027, 564, or 125 bp. 1-32 are plasmid samples; and the sample of NO.9 has a positive band of about 4.3 kb.

EXAMPLE 8

Construction of Human Serum Albumin Site-directed Integration Plasmid pTM-hSA2

The plasmid pTM-sCT2 was digested by restriction enzyme XhoI, and the sCT gene was excised to obtain plasmid framework of which the size was 7019 bp (FIG. 26). Then the plasmid pBLG-minihSA was digested by XhoI enzyme (FIG. 27) to obtain hSA expression cassette of 4015 bp. The product obtained above was linked and transferred into to competent DH5α strain, and the monoclones were selected, the bacteria was cultured with shaking, and the plasmid was extracted (FIG. 28), thereby obtaining plasmid pTM-hSA2.

The plasmid was digested by EcoRI enzyme (FIG. 29), thus obtaining target bands of 3.209 kb, 3.906 kb, and 3.872 kb. (If the hSA expression cassette was inserted in the opposite orientation, the target bands would be: 6 kb, 0.655 kb, 3.872 kb). To further verify the orientation validity of the inserted hSA gene in plasmid pTM-hSA2, based on the theoretical sequence of the plasmid, a pair of primers were designed on the 5'-end upstream of the hSA gene and within the hSA gene to conduct sequencing-detection by PCR. The sequences were shown in Table 5:

TABLE 5

| fx691-F | 5-TAGAGGAAGCAACCCCAGG-3 | SEQ ID NO.: 17 |
|---|---|---|
| fx691-R | 5-CAGCAACCAAGAAGACAGAC-3 | SEQ ID NO.: 18 |

Figure 32:
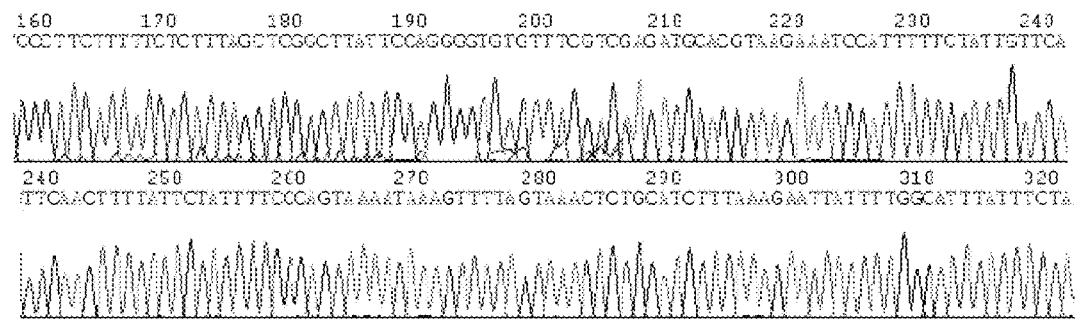
FIG. 32 shows sequencing analysis results of orientation identification of the plasmid pTM-hSA2.

The length of amplified product was 691 bp, and the annealing temperature was 58° C. The desired bands were obtained by amplification. The sequencing analysis was performed in the PCR amplified products (FIG. 30, and FIG. 32), and the results were in accordance with theoretical sequence (SEQ ID NO.:43 (FIG. 31).

The results above indicated that the plasmid pTM-sCT2 was constructed correctly.

EXAMPLE 9

Site-directed Integration Achieved by Plasmid pTM-hSA2 Mediated by TAT-Cre

Extensive extraction was performed to plasmid pTM-hSA2 by EndoFree Plasmid Maxi Kit of QIAGEN, in the 1 µg/1 µl concentration, 500 µl in total, and was packed and preserved at −20° C. for further use. And the corresponding strains were stored.

The human lysozyme transgenic goat fetal fibroblasts were recovered on the 60 mm cell petri dish, and was passaged into the 100 mm cell petri dish after grown to confluence, and the cell transfection was started when the cell density was about 80%. The number of the cells was counted after the cells were digested by trypsin, the cells were centrifuged at 1000 rpm for 5 min, and then resuspended in the electroporation buffer PBS, and the number of the cells was adjusted to $5\times10^6$-$1\times10^7$ cells/mL. 500 µl cell suspension was taken, and 12 µg of circular plasmid pTM-hSA2 filtered by 0.22 um filter was added into the cell suspension, well mixed, added to a pre-cooled 4 mm electroporation cup, stood still on ice for 5 min, and transferred into the electroporation device for electric shock in a 220V pulse voltage of and 950 µF capacitance. After electric shock, the cell suspension was put on ice for 10 min, and then transferred into the 100 mm culture plate with culture solution, cultured in 37° C., 5% $CO_2$. The cells washed with PBS for 3 times after became adherent, the OPTI-MEM was added to dilute TAT-Cre (2 µM of final concentration). After treated for 3 h, it was replaced with the normal culture solution to further culture. After 24 h, the digested cells were transferred into 6-8 100 mm cellular culture plate and puromycin (final concentration: 0.08 µg/ml) was used for pressure selection for 7 days. The monoclonal cells were transferred into 96-well cellular culture plate by using a cloning rings, and were cultured by the normal passage method. After growing to confluence in 48 wells, the cells were digested as 2 parts, in which one part was used in the integration of identification, while the other part was further cultured and frozen preserved for somatic cell cloning.

Results Identification

Figure 40:
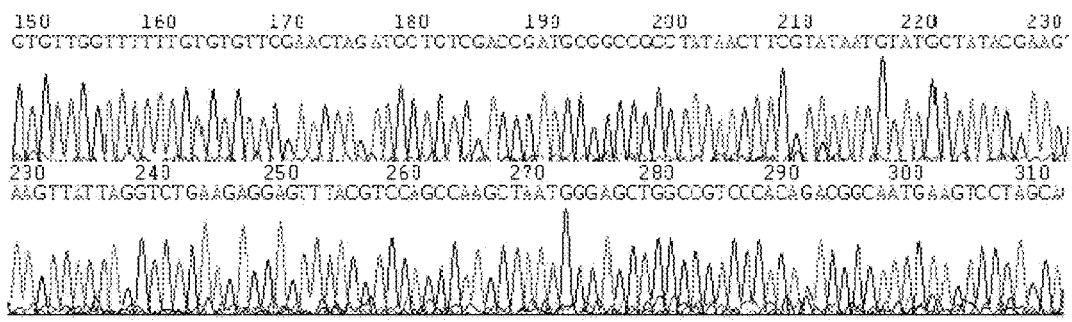
FIG. 40 shows the 3' end sequencing results of a site-directed integrated clone of human serum albumin.
Figure 41:
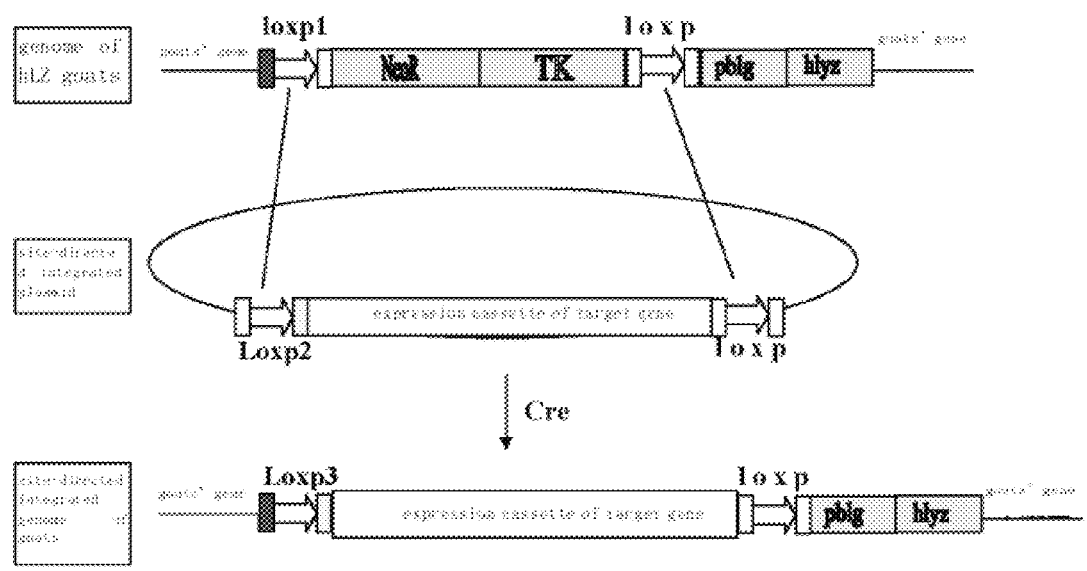
FIG. 41 shows a schematic diagram of the efficient and sited recombinant method of the present invention.

The following primers were designed to detect the 5'-end, 3'-end and the key elements of the selected clones (functional gene, screened marker gene).

rogen for sequencing analysis. The sequencing results (FIG. 39, FIG. 40) were in accordance to the theoretical sequence (FIG. 37, FIG. 38), indicating that site-directed recombinant was successfully achieved.

Figure 33:
FIG. 33 shows the 5' end detection electrophoretogram of selected clonal cell lines. M1 is D2000 marker; 1, 2, 8-24 are the 5' end detection electrophoretogram of selected clones, wherein 11, 12, 14, 20, 21, 1, and 2 are positive; 26 and 5 are the positive controls; and 27 and 6 are the negative controls.
Figure 34:
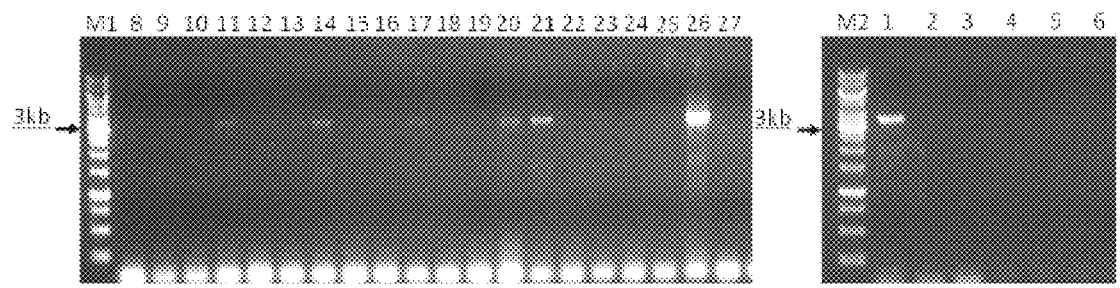
FIG. 34 shows the 3' end detection electrophoretogram of selected clonal cell lines. M1 is D2000; 1-4 and 8-25 are the 3' end detection electrophoretogram of selective clones, wherein 11, 14, 17, 20, 21, and 1 are positive; 26 and 5 are the positive controls; and 27 and 6 are the negative controls.
Figures 35, 36, 37:
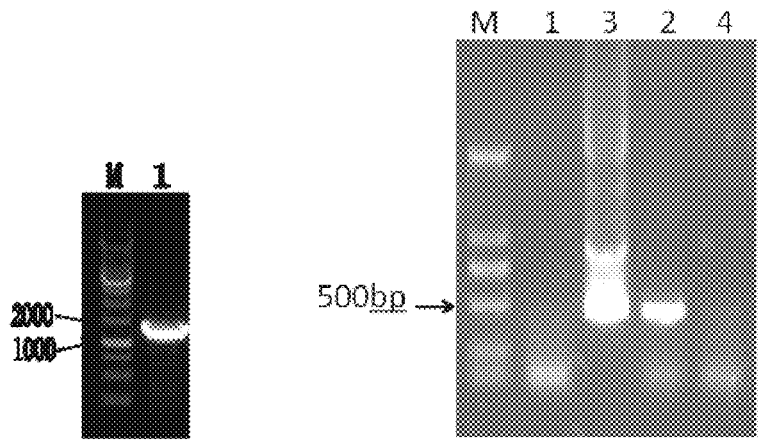
FIG. 35 shows the detection pattern of functional genes in the screened clonal cell lines. M is 1 kb DNA ladder; 1 is the detection pattern for screening clone selective gene.
FIG. 36 shows detection pattern of selective gene in the screened clonal cell lines. M is D2000; 1 and 2 are detection pattern for screening selective gene; 1 is positive clone; 3 is the positive control; and 4 is the negative control.
FIG. 37 shows the 5' end recombinant theoretical sequence of a site-directed recombinant clone of human serum albumin (SEQ ID NO.:44).
Figures 38, 39:
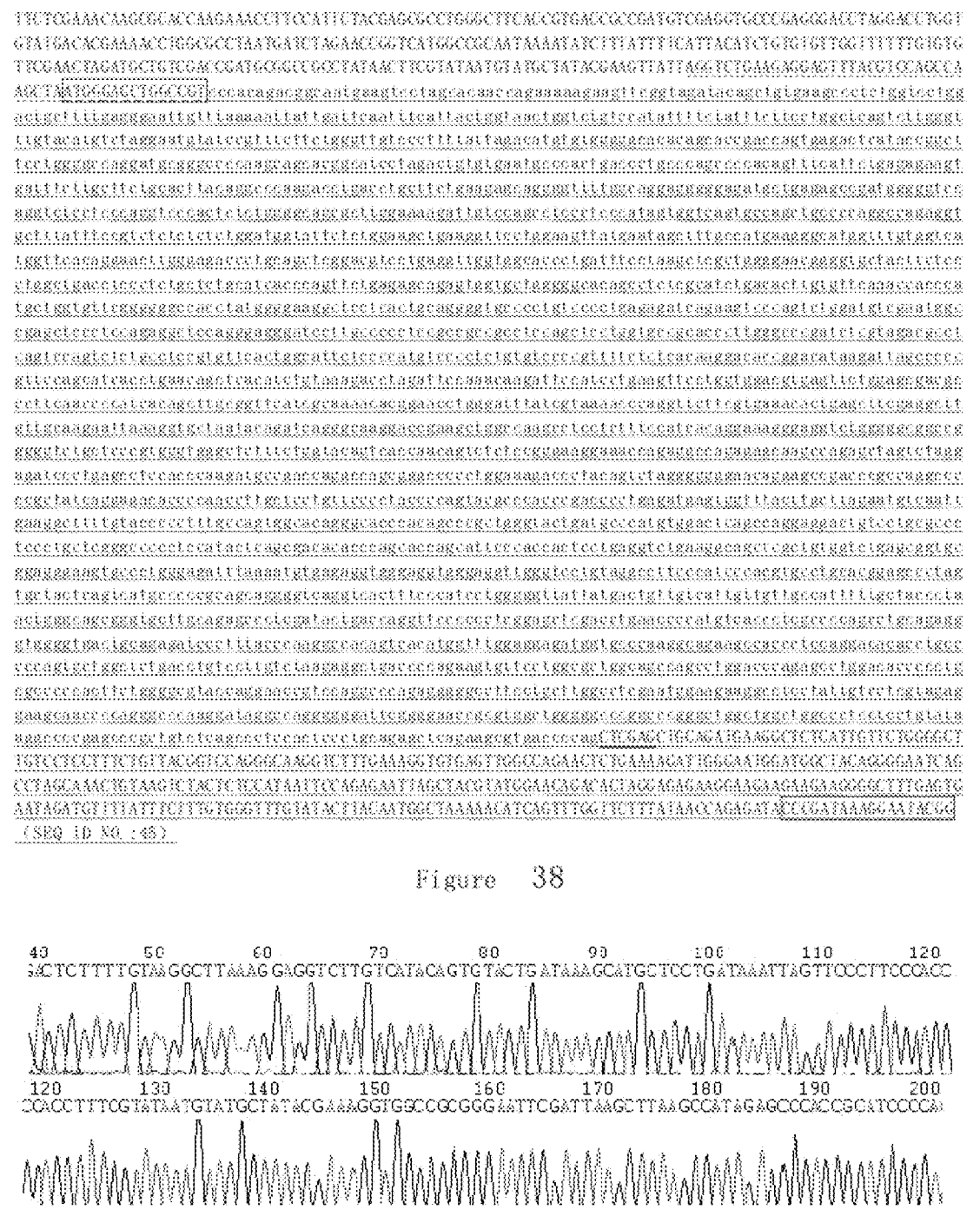

FIG. 33 shows the 5' end detection electrophoretogram of the selected clonal cell lines; wherein M1 is D2000 marker; 1, 2, and 8-24 are the 5' end detection electrophoretograms of selected clonal cell lines, wherein 11, 12, 14, 20, 21, 1, and 2 are positive; 26 and 5 are the positive controls; and 27 and 6 are the negative controls. FIG. 34 shows the 3' end detection electrophoretogram of selected clonal cell lines; wherein M1 is D2000; 1-4 and 8-25 are the 3' end detection electrophoretogram of selective clonal cell line, wherein 11, 14, 17, 20, 21, and 1 are positive; and 26 and 5 are the positive controls; and 27 and 6 are the negative controls. FIG. 35 shows the detection pattern of functional genes in the screened the clonal cell lines, wherein M is 1 kb DNA ladder; 1 is the detection pattern for screening clone selective gene. FIG. 36 shows detection pattern of selective gene in the screened clonal cell lines; wherein M is D2000; 1 and 2 are detection pattern for screening selective gene, 1 is positive clone; 3 is the positive control; and 4 is the negative control. FIG. 37 shows the 5'-end recombinant theoretical sequence of a site-directed recombinant clone of human serum albumin. FIG. 38 shows the 3'-end recombinant theoretical sequence of a site-directed recombinant clone of human serum albumin.

TABLE 6

| | primers | Length of amplified fragment (bp) | location |
|---|---|---|---|
| 5'-end detection | sy1126-F: CAAGCCACCTAACCTCAC SEQ ID NO.: 19 | 1126 | genome of goat |
| | sy1126-R: TGCTATGCCAAAGTGTTC SEQ ID NO.: 20 | | hsA gene |
| 3'-end detection | xy3365-F: TTCTCGAAACAAGCGCAC SEQ ID NO.: 21 | 3365 | expression cassette of puro |
| | xy3365-R: CCGTATTCCTTTATCGGGTAT SEQ ID NO.: 22 | | genomic DNA of goat |
| detection of Neo | F: 5-CTGCTATTGGGCGAAGTGC-3 SEQ ID NO.: 23 | 469 | gene Neo |
| | R: 5-CGGCGATACCGTAAAGCAC-3 SEQ ID NO.: 24 | | gene Neo |
| detection of hsA | F: 5-GCTGCGAAATCATCCATA-3 SEQ ID NO.: 25 | 1338 | gene hsA |
| | R: 5-TGACAACCCAAACCTCCCC-3 SEQ ID NO.: 26 | | gene hsA |

25 clones of plasmid pTM-hSA2 transferred by rhlyzGFC were obtained in total, of which the genome was extracted, and the detections were made for 5'-end (FIG. 33), 3'-end (FIG. 34), functional gene (FIG. 35) and selective gene (FIG. 36) by PCR amplification method (pre-denaturation at 4° C. for 5 min; denaturated at 94° C. for 30 s; renaturated for 30 s (the annealing temperature was indicated in Table 6), extended at 72° C. for 30 s, 30 cycles in total; finally extended at 72° C. for 5 min). The results showed that there were 5 positive clones 1, 11, 14, 20, and 21. The site-directed recombinant efficiency was 5/25=20%. The selected positive clones were amplified, and the products were sent to Invit-

EXAMPLE 10

Somatic Cell Cloning of Site-directed Integration Cell Clone

1. Preparation of Oocytes and the Synchronization of Receptor Goats

The female goats useful as oocyte donors were selected and intramuscular injected with PG at 0.1 mg/goat, the second PG injection was performed after 10 to 14 days intervals, and the superovulation was begun 10 to 13 days after the second PG injection, that is, firstly, intramuscular injected with FSH, which was divided into 6 times, twice a day, and the daily amount was 100 IU, 80 IU, 80 IU. PG (0.1 mg/goat) was injected simultaneously to the last FSH injection, and LRH was injected 24 hours after, 25 µg/time, and the oocytes were recovered 26-28 hours after LRH injection.

In order to synchronize with the donor goats which provided oocytes, the receptor goats were PG intramuscular injected in twice at the intervals of 9-11 days. 24 hours after superovulation PG injection to the donor goats, the receptor goats were also injected with PG, the time and dose of LRH injection for the receptors were the same to those of donor goats.

Oviducts were exposed by surgery, the eggs were washed with F-10 nutrient solution, and inspected by stereoscope. Granulosa cells were digested with hyaluronidase, washed 4-5 times with M16, and cultured in the M16 square cup for further use.

2. Starvation Treatment of Nucleated Cells

Pre-starvation cells were seeded on 35 mm petri dish. When the confluence of cells reached about 70%-75%, the nutrient solution was sucked out, and the DMEM medium containing 0.5% FCS was added. After starvated for 5 days, the cells were digested and collected by conventional method, and then preserved in the −85° C. refrigerator. Six days before nuclear transplantation experiments, 2 small tubes of cells were taken out to recover and seeded into the 4-well plate. Starvation was conducted after re-cultured for 2 or 3 days, and the starvation method was indicated above.

3. Preparation and Activation of Reconstructed Eggs

The oocytes were washed 3 times with M16-Hepes (Hepes 2.8 mg/ml, CB 7.5 µg/ml), treated in M16-Hepes (comprising 7.5 µg/ml of CB) for 10 min. Meanwhile, the cultured cells were digested by trypsin, and dispersed into single cells. The oocytes and donor cells were simultaneously transferred into 1 ml M16-Hepes (containing CB) on sterilized glass slides, the nuclei was removed under microscope, and the donor cells were sucked in, injected from the original incision into perivitelline space, thus making it attached tightly to cytoplasmic membrane, and was fused by electrical stimulation, the fusion matrix was a solution with 0.3 nM mannitol, 0.05 mM calcium chloride, 0.1 mM magnesium sulfate, 0.5% BSA. The fusion condition was DC600-610 v/cm, of which the pulse duration time was 80 µs, and the stimulation was continuously stimulated for three times. Fused fetus was cultured in M16 solution for 5 h, treated in M16 solution comprising 5 µM ionomycin and 7.5 µg/ml CB for 5 min, and then treated in M16 solution comprising 2 mM 6-DMAP and 7.5 µg/ml CB for 5 h, then transferred into in M16 culture solution and cultured until it was embedded or transplanted.

4. The Embed, Recovery of Reconstructed Eggs and the Transplantation of Developing Embryos.

Reconstructed eggs were embedded in 1% Agarose, transplanted to oviduct, and the strip was washed out after cultured for 5 days in vivo. The embryo inside the strip was stripped out, and the morula and blastocyst were selected and transplanted to the uterus of recipient goats, and the developmental rate of morula and blastocyst was counted.

5. Developmental Rate and Pregnancy Rate of Reconstructed Eggs.

For salmon calcitonin site-directed integration cells, there were 39 egg donor goats in total, and 462 eggs were taken; 423 eggs were used for nuclei-transplantation, and there were 387 fused eggs in total, of which the fusion rate was 91.56% (387/423). 355 reconstructed embryoes were activated, 277 were embedded, and 127 embryoes were directly transplanted. After embedded, 216 embryoes were recovered, recovery rate was 95.15%; the number of cleaved was 203, of which the cleavage rate was 93.98%, the number of normal fissured was 114, which was 52.78% of the number of total fissured. 48 morulas were obtained, of which the morula rate was 22.22%. 27 receptors were transplanted into the uterus; 12 receptors were directly transplanted into oviduct. Each was transplanted with 10-12 reconstructed embryoes. 39 receptors were transplanted in total. The results of 30-35 days B ultrasonic examination: 9 receptors of 27 receptors transplanted with morula and blastocyst into the uteruses were pregnant (of which pregnant rate was 33.3%); 11 receptors of the 12 receptors transplanted with 1-2 cells into the oviduct were pregnant (91.7% of pregnant rate). 20 receptors were pregnant out of 39 receptors in total (51.3% of pregnant rate).

For site-directed integration cells of serum albumin expression cassette, there were 32 egg donors in total, and 441 eggs were taken; 401 eggs were nuclei-transplanted, and there were 375 eggs fused in total, of which the fusion rate was 92.27% (346/375). 338 reconstructed embryoes were activated, and 338 embryoes were directly transplanted. 35 receptors were directly transplanted into oviduct, while each of 10-12 reconstructed embryoes was transplanted. 32 days after transplantation, the results of -B ultrasonic examination showed that 20 receptors were pregnant, of which the pregnant rate was 57.1%.

The above results showed that the effect of somatic cell cloning for the site-directed integration cells was normal, in which indexes of all the parts such as fusion rate of reconstructed embryoes, cleavage rate, developmental rate of morula and blastocysts and pregnant rate of receptors were consistent with the efficiency of non-targeted integrated somatic cell cloning. It indicated that there were no significantly adverse effect on the cloning of somatic cells treated by site-directed integration method during the afterward somatic cell cloning, and the method is useful to prepare somatic cell cloned goats.

EXAMPLE 11

Preparation of Human Lactoferrin Transgenic Site-directed Integration Goats

1. Construction of Human Lactoferrin Site-directed Integration Framework pTM-hLf.

Human lactoferrin mini gene was artificially synthesized. The gene included cDNA sequence of human lactoferrin and the fifteenth intron sequence of human lactoferrin (SEQ ID NO.: 32 and FIG. 43), human lactoferrin site-directed integration framework pTM-hLf was constructed and prepared based on the method of Example 8.

2. The Preparation of pTM-hLf Integrated Cells.

Figure 44:
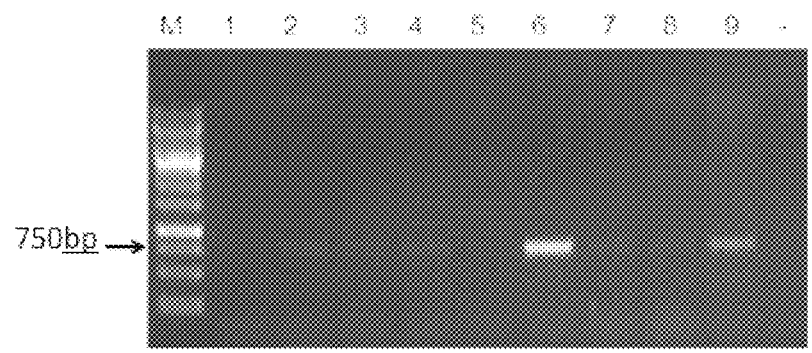
FIG. 44 shows an identification of 5'-end of hLf gene in a site-directed integration in the clonal cell line. The lanes are as followed: M is 1 kb DNA Marker; Nos. 1-9 shows 5'-end sited integration in the detected clonal cell line of hLf; "−" is the negative control.
Figure 45:
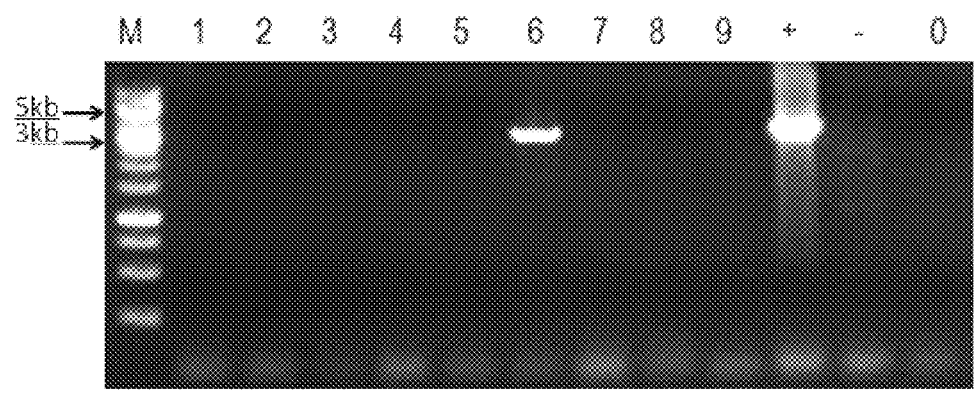
FIG. 45 shows an identification of 3'-end of hLf gene in a site-directed integration in the clonal cell line. The lanes are as followed: M is 1 kb DNA Marker; Nos. 1-9 are 5'-end sited integration in the detected clonal cell line of hLf; "+" is the positive control, "−" is the negative control, and 0 is blank control.
Figure 46:
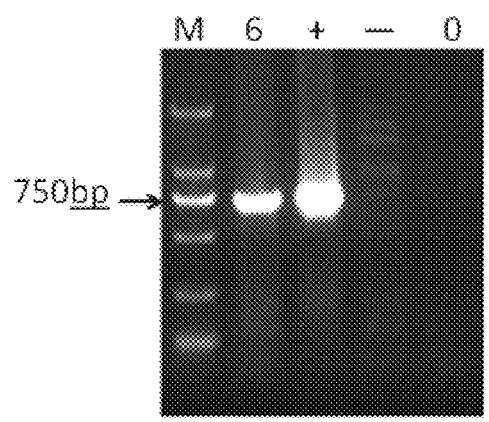
FIG. 46 shows an identification of hLf gene integration in the clonal cell line. Lanes are as follows: No. 6 is a selected clonal cell line screened with puromycin for 8 days, "−" means normal goat, "+" is the positive control, 0 is blank control, and M is DL2000 Marker.
Figure 47:
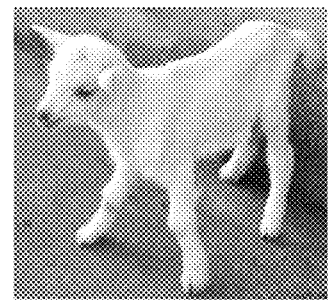
FIG. 47 shows hLf site-specific integration of transgenic cloned sheep.
Figure 48:
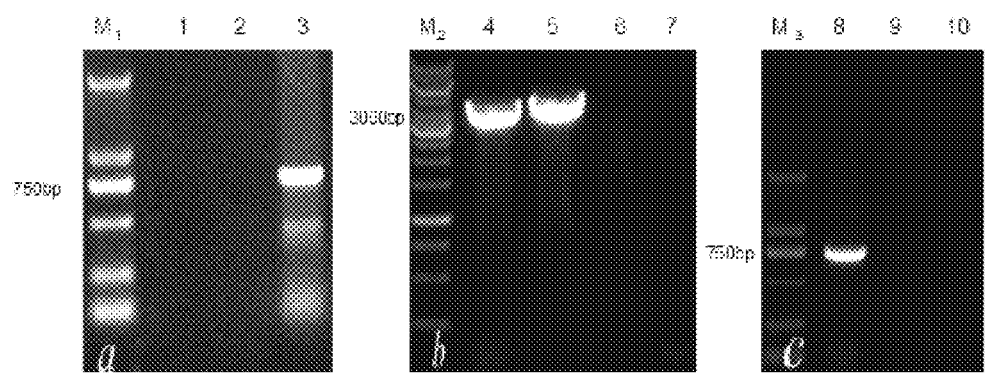
FIG. 48 shows an identification of hLf site-specific (or site-directed) integration in a transgenic cloned sheep. Wherein, "a" shows 5'-end of transgenic detection, in which M1 is DL2000 Marker, 1 is blank control, 2 is negative control, and 3 is hLF clonal goat; "b" shows 3'-end of transgenic detection in which M2 is 1 kb DNA Marker, 4 is hLF clonal goat, 5 is a cellular positive control, 6 is a negative control, and 7 is blank control; "c" shows the detection of Lf functional gene in which M3 is DL2000 Marker, 8 is clonal goat, 9 is a negative control, and 10 is blank control.

Fibroblasts of goat ear were co-transfected by pTM-hLf and plasmid pBS185 expressing Cre at a molar ratio of 1:1, selected with 0.08 µg/mL of puromycin for 8-10 days. 45 monoclones were selected onto 96-well plates, and further cultured on 6-well plates. Meanwhile, 9 clones grown in good condition were detected with test primers, wherein, 1 cell line hLf-hlz-6 was identified as site-directed integration cell (see FIG. 44, FIG. 45 and FIG. 46). Identifying primers were shown in Table 7.

TABLE 7 primers used in the process of hLF transgenic site-directed integration of goats

| detection regions | primers' name and the sequence thereof (5'-3') | SEQ ID NO.: | annealing temperature | length of amplified fragment |
|---|---|---|---|---|
| 5'-end detection | P1-F ACCAGTTAGCTAGGTGGGCAT | 33 | 58° C. | 760 bp |
| | P1-R GGTTTTCTCAGGGCTGTTCT | 34 | | |
| 3'-end detection | P2-F TTCTGACACTAGCGCCACC | 35 | 58° C. | 3365 bp |
| | P2-R GCCAGCTCCCATTAGCTTG | 36 | | |
| integrated detection of LF | P3-F GAAGTCTACGGGACCGAAAG | 37 | 58° C. | 734 bp |
| | P3-R TAGCCGGAGCCAAGGTACA | 38 | | |

The homology of sequencing results of site-directed integration identified 3' and 5' ends of the PCR products were both of >99% homology with that of theoretical sequence, and both ends comprised loxP sequence, which indicated that site-directed integration was accurate. Therefore, one cell line (marked as NO.6 cell of hLf-hlz-6) was selected from the site-directed cells which were identified as accurate for performing the subsequent somatic cell cloning experiments.

3. Preparation of hLF Site-directed Integrated Somatic Cell Cloned Goats

The cell of hLf-hlz-6 was in good condition, used for somatic cell cloning. 774 normal goat oocytes were used, and 712 oocytes were nuclei transplanted, while 606 oocytes were fused in total, and of which the fusion rate was 77.72% (471/606). 48 receptor goats were transplanted. After transplanted for 30 days, B-pregnancy check showed that 10 receptor goats were pregnant, and the pregnant rate was 20.83%.

3 live clonal goats were finally obtained, and was detected with the primers shown in Table 1, the results indicating that the goats were positive transgenic site-directed integrated.

EXAMPLE 12

Detection of Human Serum Albumin Expression of Transgenic Goats

In this embodiment, human Serum Albumin gene Targeted Transgenic Goat (hSA-GTTG) was lactation stimulated, and the expression amount of human serum albumin (hSA) in the milk of the hSA-GTTG was detected. The effectiveness of the targeted system was determined. The process of detection and the results thereof was listed as followed:

1. Lactation Stimulation of Male Goats hSA-GTTG

Primary hSA-GTTG transgenic goats were selected, and estradiol benzoate (2 mg) and progesterone (20 mg) were intramuscular injected twice a day during 7 days in total. Then reserpine (0.5 mg) was intramuscular injected on Day 8, 10, 12, and 14 respectively. The milk was collected on Day 12, which was the first day milk, and preserved at −20° C. ready for use. hSA-GTTG goats were lactation stimulated by traditional lactation stimulation method, about 120 µl milk was collected in 4 days, of which the average was 40 µl/day.

2. Determination of Activity Unit for the Lysozyme in Milk

Firstly, the micrococcus lysodeikticus (available from Sigma, M0192) was formulated with 0.18M sodium acetate (pH5.5) buffer into 0.8 mg/ml substrate testing liquid suspension (OD450: 0.6-1.0). 2 µl milk was added into 3 ml substrate testing liquid, and the variation of OD450 light absorption was measured. Every 0.001 decrease was defined as an activity unit. The tested sample included: milk of hSA-GTTG male goats, human lysozyme transgenic goats and normal goats.

After lysozyme activity was identified, in the milk of hSA-GTTG goats, there were 92.6 activity units per µl, and 55.6 activity units in the ordinary milk of human lysozyme transgenic goats. The activity unit in the normal goats' milk was negative value. The detailed results were shown in Table 8.

TABLE 8

Determination of activity unit of lysozyme in hSA milk

| | non-milk control | normal goat milk | lysozyme milk | hSA milk |
|---|---|---|---|---|
| OD$_{450}$ of T$_{0\ min}$ | 0.8509 | 0.8814 | 0.8521 | 0.8141 |
| OD$_{450}$ of T$_{1\ min}$ | 0.8495 | 0.8844 | 0.7395 | 0.6275 |
| ΔT$_{0\ min}$ − T$_{1\ min}$ | 0.0014 | −0.003 | 0.1126 | 0.1866 |
| activity unit/µl milk | / | −3 | 55.6 | 92.6 |

The activity unit number of lysozyme in hSA-GTTG milk was 1.665 times larger than that in human lysozyme transgenic milk, which indicated that there was no significantly adverse effect on the expression of lysozyme framework after the hSA expression cassette was integrated into the lysozyme integration site. Although the activity of lysozyme in the hSA-GTTG milk was improved, due to lactation stimulation for male goats, the protein content in milk was increased. Therefore, it was not determined that the expression cassette of human lysozyme was improved after integration.

3. SDS-PAGE Electrophoresis and Detection of Western-blotting

The goat milk was 10-fold diluted with distilled water, and an equal volume of 2× SDS gel loading buffer was added, incubated at 65° C. for 15 min. 5 µl was taken out for SDS-PAGE Electrophoresis, the concentration of stacking gel was 4%, the concentration of separation gel was 7.5%, and the constant voltage was 100V. An anti-mouse anti-hSA monoclonal antibody (Abcam, ab10241) was used as the first antibody for Western-blotting analysis (1:1000); the second antibody was HRP-labeled rabbit anti-mouse IgG (Abcam, ab97046) (1:2000), finally colorated with DAB.

Figure 49:
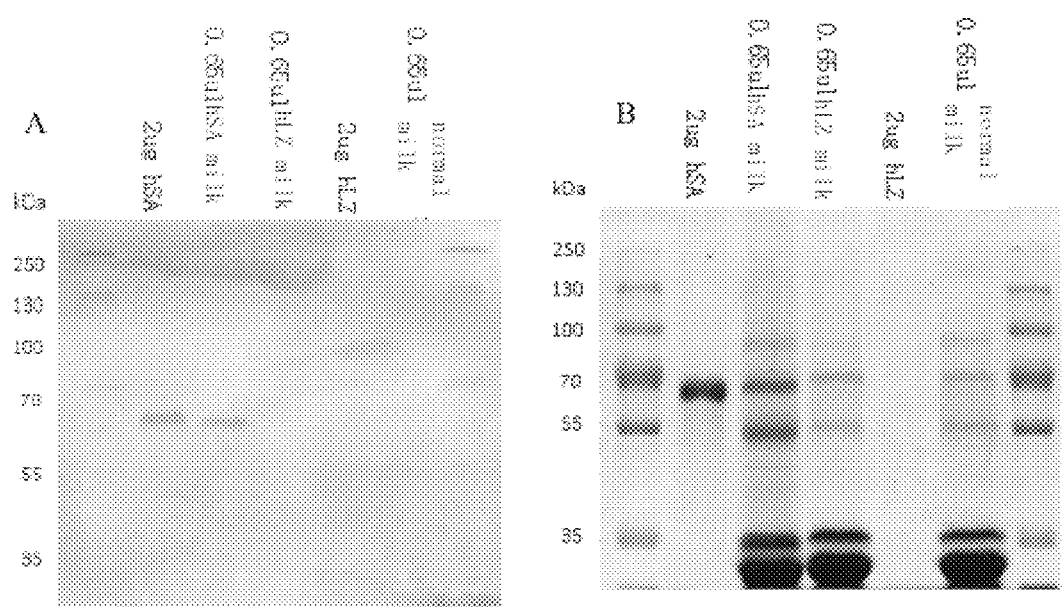
FIG. 49 shows detection of SDS-PAGE electrophoresis and Western-blotting of the hSA-GTTG goat's milk. Wherein, "A" shows analysis results of SDS-PAGE; and "B" shows Western-blotting results.

The results of SDS-PAGE and Western-bloting both indicated that there was clear band in the hSA-GTTG milk of which the size was close to that of natural hSA (FIG. 49), which showed that hSA was expressed effectively.

4. Estimation of the Expression of Recombinant hSA in Milk

Preparation of standard curve. The hSA standards were added to normal goat's milk at a concentration of 2 mg/ml, the normal goat's milk was used as gradient to dilute hSA to 1 mg/ml, 0.5 mg/ml, 0.25, 0.125 mg/ml and 0.0625 mg/ml of concentration. The hybridization signal was obtained by Western-bloting or Slot-bloting method, the hybridization signal was scanned by Bio-1D software, and the standard curve was prepared. The content of hSA in milk was calculated by the hybridization signal of hSA-GTTG milk sample based on the standard curve.

Figure 50:
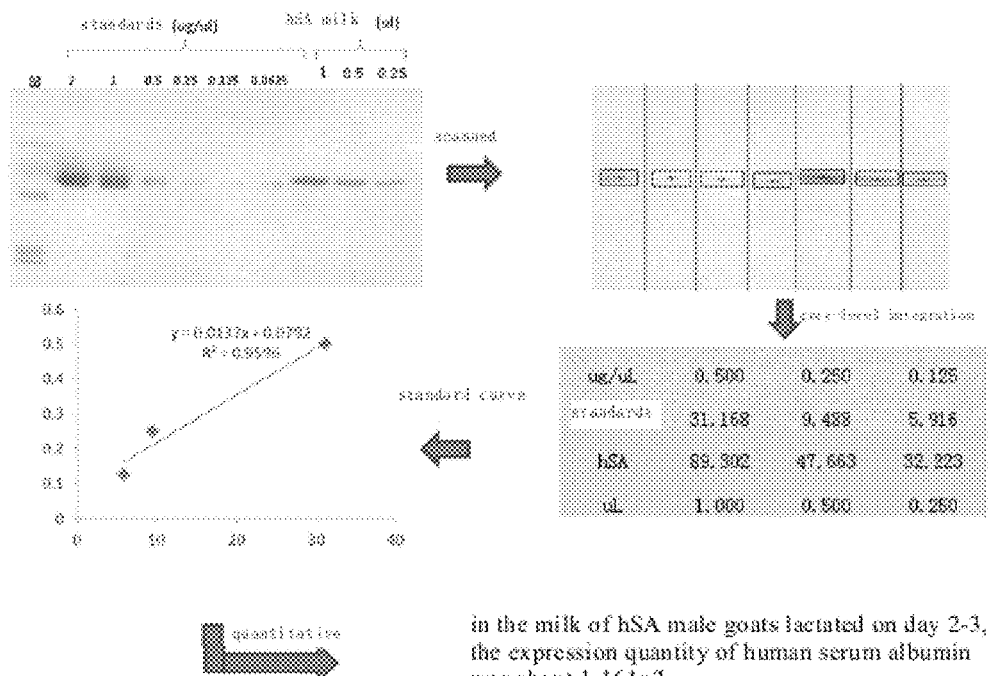
FIG. 50 shows a hSA content detection in hSA-GTTG goat's milk on the third day of lactation.
Figure 51:
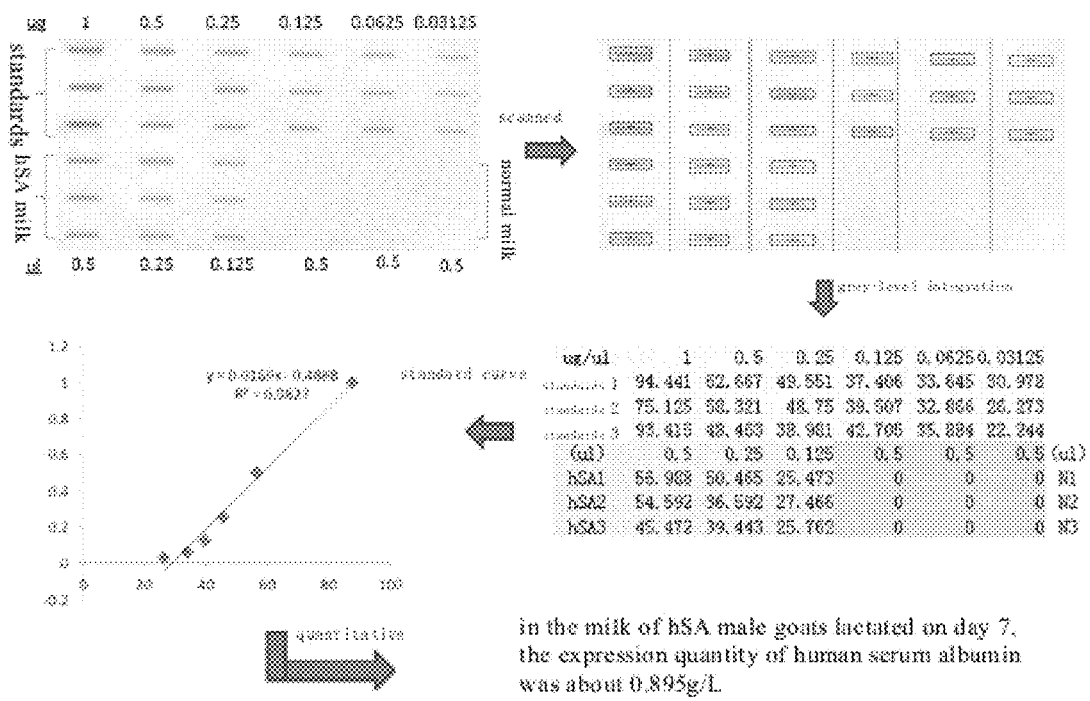
FIG. 51 shows a hSA content detection in hSA-GTTG goat's milk on the seventh day of lactation.

After tested, the content of hSA in the goat's milk of hSA-GTTG lactated on day 3 was about 1.464 g/L (FIG. 50). The expression quantity of hSA in the milk lactated on day 7 was about 0.895 g/L (FIG. 51).

Moreover, although the transgenic goats simultaneously carried exogenous human lysozyme and human serum albumin gene, expression of either protein was not mutually interfered.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A mutant loxP element for the improvement of integration specificity and integration efficiency in cre-loxp integration system, which consists essentially of the sequence as shown in SEQ ID NO.: 30.

2. A construct for the improvement of integration specificity and integration efficiency in cre-loxp integration system, wherein the construct comprises from 5' to 3' the following elements:
   (a) a mutant loxP element consisting essentially of the sequence as shown in SEQ ID NO.: 30;
   (b) an expression cassette of an exogenous gene and/or an expression cassette of a selective gene for screening;
   (c) a wild-type loxP element having a sequence as shown in SEQ ID NO.: 28; wherein element (a) and element (c) are interchangeable in position wherein the exogenous gene is selected from the group consisting of: lysozyme gene, salmon calcitonin gene, lactoferrin gene, and serum albumin gene.

3. The construct according to claim 2 wherein element (a) and element (c) are placed in the same orientation.

4. The construct according to claim 2 disposed within a vector.

5. The construct according to claim 2 disposed within a host cell.

6. The construct according to claim 5, wherein the host cell is a goat adult somatic cell, a goat fetal somatic cell, or a goat embryonic stem cell.

7. The construct according to claim 5, wherein the construct is introduced into the host cell by a method selected from the group consisting of: homologous recombination method, microinjection, electroporation, lipofection, calcium phosphate precipitation, virus infection method, and sperm-mediated gene transfer technique.

8. A method for the improvement of integration specificity and integration efficiency in Cre-loxp integration system comprising the following steps:
   (i) transforming a cell in the presence of Cre recombinase using a vector, wherein the vector comprises from 5' to 3' the following elements:
   (a) a mutant loxP element consisting essentially of the sequence as shown in SEQ ID NO.: 30
   (b) an expression cassette of an exogenous gene and/or an expression cassette of a selective gene for screening;
   (c) a wild loxP element having a sequence as shown in SEQ ID NO.: 28;
   wherein element (a) and element (c) are interchangeable in position,
   (ii) placing the transformed cell into an animal, thereby obtaining a transgenic animal, and improving the integration specificity and integration efficiency in Cre-loxp integration system.

9. A method for preparing a transgenic animal comprising the following steps:
   (i) transforming a cell in the presence of Cre recombinase using a vector, wherein the vector comprises from 5' to 3' the following elements:
   (a) a mutant loxP element comprising a sequence as shown in SEQ ID NO.: 30;
   (b) an expression cassette of an exogenous gene and/or an expression cassette of a selective gene for screening;
   (c) a wild loxP element having a sequence as shown in SEQ ID NO.: 28;
   wherein element (a) and element (c) are interchangeable in position,
   (ii) placing the transformed cell into an animal, thereby obtaining a transgenic animal wherein step (i) comprises a step of:
   co-transforming the cell using a Cre enzyme expression vector and a vector which comprises from 5' to 3' the following elements:
   (a) a mutual loxP element consisting essentially of the sequence as shown in SEQ ID NO.: 30, and
   (b) an expression cassette of an exogenous gene and/or an expression cassette of a selective gene for screening and
   (c) a wild loxP element having a sequence as shown in SEQ ID NO.:28 wherein element (a) and element (c) are interchangeable in position.

10. The method according to claim 8, wherein step (i) comprises a step of:
   administering a TAT-Cre recombinant protein having a cell-penetrating activity to the transformed cell, wherein a chromosome of the cell is genetically integrated with the vector comprising a construct comprising from 5' to 3' the following elements:
   (a) a mutant loxP element comprising a sequence as shown in SEQ ID NO.: 30;
   (b) an expression cassette of an exogenous gene and/or an expression cassette of a selective gene for screening;
   (c) a wild-type loxP element having a sequence as shown in SEQ ID NO.: 28;
   wherein element (a) and element (c) are interchangeable in position.

* * * * *

SEQUENCE LISTING

```
<160> NUMBER OF SEQ ID NOS: 40

<210> SEQ ID NO 1
<211> LENGTH: 24
<212> TYPE: DNA
<213> ORGANISM: Artificial sequence
<220> FEATURE:
<223> OTHER INFORMATION: oligonucleotide

<400> SEQUENCE: 1
caatcgtatg cttctgctat gttc                                              24

<210> SEQ ID NO 2
<211> LENGTH: 21
<212> TYPE: DNA
<213> ORGANISM: Artificial sequence
<220> FEATURE:
<223> OTHER INFORMATION: oligonucleotide

<400> SEQUENCE: 2
caatgttacc ctatcgtggc c                                                 21

<210> SEQ ID NO 3
<211> LENGTH: 23
<212> TYPE: DNA
<213> ORGANISM: Artificial sequence
<220> FEATURE:
<223> OTHER INFORMATION: oligonucleotide

<400> SEQUENCE: 3
tacatttgag gacctggcag agc                                               23

<210> SEQ ID NO 4
<211> LENGTH: 22
<212> TYPE: DNA
<213> ORGANISM: Artificial sequence
<220> FEATURE:
<223> OTHER INFORMATION: oligonucleotide

<400> SEQUENCE: 4
tcctaccact ttgggaggct ga                                                22

<210> SEQ ID NO 5
<211> LENGTH: 30
<212> TYPE: DNA
<213> ORGANISM: Artificial sequence
```

<220> FEATURE:
<223> OTHER INFORMATION: oligonucleotide

<400> SEQUENCE: 5
ttgcggccgc gataaggatc cgtttgcgta         30

<210> SEQ ID NO 6
<211> LENGTH: 30
<212> TYPE: DNA
<213> ORGANISM: Artificial sequence
<220> FEATURE:
<223> OTHER INFORMATION: oligonucleotide

<400> SEQUENCE: 6
ttgcggccgc atcggtcgac agcatctagt         30

<210> SEQ ID NO 7
<211> LENGTH: 20
<212> TYPE: DNA
<213> ORGANISM: Artificial sequence
<220> FEATURE:
<223> OTHER INFORMATION: oligonucleotide

<400> SEQUENCE: 7
caagccacct aacctcactg         20

<210> SEQ ID NO 8
<211> LENGTH: 18
<212> TYPE: DNA
<213> ORGANISM: Artificial sequence
<220> FEATURE:
<223> OTHER INFORMATION: oligonucleotide

<400> SEQUENCE: 8
tcgtagagga agcaaccc         18

<210> SEQ ID NO 9
<211> LENGTH: 19
<212> TYPE: DNA
<213> ORGANISM: Artificial sequence
<220> FEATURE:
<223> OTHER INFORMATION: oligonucleotide

<400> SEQUENCE: 9
ttctgacact agcgccacc         19

<210> SEQ ID NO 10
<211> LENGTH: 19
<212> TYPE: DNA
<213> ORGANISM: Artificial sequence
<220> FEATURE:
<223> OTHER INFORMATION: oligonucleotide

<400> SEQUENCE: 10
gccagctccc attagcttg         19

<210> SEQ ID NO 11
<211> LENGTH: 19
<212> TYPE: DNA
<213> ORGANISM: Artificial sequence
<220> FEATURE:
<223> OTHER INFORMATION: oligonucleotide

<400> SEQUENCE: 11
ctgctattgg gcgaagtgc         19

<210> SEQ ID NO 12
<211> LENGTH: 19
<212> TYPE: DNA
<213> ORGANISM: Artificial sequence
<220> FEATURE:
<223> OTHER INFORMATION: oligonucleotide

<400> SEQUENCE: 12
cggcgatacc gtaaagcac                                               19

<210> SEQ ID NO 13
<211> LENGTH: 22
<212> TYPE: DNA
<213> ORGANISM: Artificial sequence
<220> FEATURE:
<223> OTHER INFORMATION: oligonucleotide

<400> SEQUENCE: 13
acctactcag acaatgcgat gc                                           22

<210> SEQ ID NO 14
<211> LENGTH: 20
<212> TYPE: DNA
<213> ORGANISM: Artificial sequence
<220> FEATURE:
<223> OTHER INFORMATION: oligonucleotide

<400> SEQUENCE: 14
cggagcccta gtgctactca                                              20

<210> SEQ ID NO 15
<211> LENGTH: 18
<212> TYPE: DNA
<213> ORGANISM: Artificial sequence
<220> FEATURE:
<223> OTHER INFORMATION: oligonucleotide

<400> SEQUENCE: 15
ttacggcgct aaggatga                                                18

<210> SEQ ID NO 16
<211> LENGTH: 21
<212> TYPE: DNA
<213> ORGANISM: Artificial sequence
<220> FEATURE:
<223> OTHER INFORMATION: oligonucleotide

<400> SEQUENCE: 16
ctttacagtg acaatgacgg c                                            21

<210> SEQ ID NO 17
<211> LENGTH: 19
<212> TYPE: DNA
<213> ORGANISM: Artificial sequence
<220> FEATURE:
<223> OTHER INFORMATION: oligonucleotide

<400> SEQUENCE: 17
tagaggaagc aaccccagg                                               19

<210> SEQ ID NO 18
<211> LENGTH: 20
<212> TYPE: DNA
<213> ORGANISM: Artificial sequence
<220> FEATURE:
<223> OTHER INFORMATION: oligonucleotide

```
<400> SEQUENCE: 18
cagcaaccaa gaagacagac                                               20

<210> SEQ ID NO 19
<211> LENGTH: 18
<212> TYPE: DNA
<213> ORGANISM: Artificial sequence
<220> FEATURE:
<223> OTHER INFORMATION: oligonucleotide

<400> SEQUENCE: 19
caagccacct aacctcac                                                 18

<210> SEQ ID NO 20
<211> LENGTH: 18
<212> TYPE: DNA
<213> ORGANISM: Artificial sequence
<220> FEATURE:
<223> OTHER INFORMATION: oligonucleotide

<400> SEQUENCE: 20
tgctatgcca aagtgttc                                                 18

<210> SEQ ID NO 21
<211> LENGTH: 18
<212> TYPE: DNA
<213> ORGANISM: Artificial sequence
<220> FEATURE:
<223> OTHER INFORMATION: oligonucleotide

<400> SEQUENCE: 21
ttctcgaaac aagcgcac                                                 18

<210> SEQ ID NO 22
<211> LENGTH: 21
<212> TYPE: DNA
<213> ORGANISM: Artificial sequence
<220> FEATURE:
<223> OTHER INFORMATION: oligonucleotide

<400> SEQUENCE: 22
ccgtattcct ttatcgggta t                                             21

<210> SEQ ID NO 23
<211> LENGTH: 19
<212> TYPE: DNA
<213> ORGANISM: Artificial sequence
<220> FEATURE:
<223> OTHER INFORMATION: oligonucleotide

<400> SEQUENCE: 23
ctgctattgg gcgaagtgc                                                19

<210> SEQ ID NO 24
<211> LENGTH: 19
<212> TYPE: DNA
<213> ORGANISM: Artificial sequence
<220> FEATURE:
<223> OTHER INFORMATION: oligonucleotide

<400> SEQUENCE: 24
cggcgatacc gtaaagcac                                                19

<210> SEQ ID NO 25
```

```
<211> LENGTH: 18
<212> TYPE: DNA
<213> ORGANISM: Artificial sequence
<220> FEATURE:
<223> OTHER INFORMATION: oligonucleotide

<400> SEQUENCE: 25
gctgcgaaat catccata                                              18

<210> SEQ ID NO 26
<211> LENGTH: 19
<212> TYPE: DNA
<213> ORGANISM: Artificial sequence
<220> FEATURE:
<223> OTHER INFORMATION: oligonucleotide

<400> SEQUENCE: 26
tgacaaccca aacctcccc                                             19

<210> SEQ ID NO 27
<211> LENGTH: 4015
<212> TYPE: DNA
<213> ORGANISM: Homo sapiens

<400> SEQUENCE: 27
ctcgaggccg ccaccatgaa gtgggtaacc tttatttccc ttcttttct ctttagctcg      60 gcttattcca ggggtgtgtt tcgtcgagat gcacgtaaga aatccatttt tctattgttc    120
aacttttatt ctattttccc agtaaaataa agttttagta aactctgcat ctttaaagaa    180 ttatttggc atttatttct aaaatggcat agtatttgt atttgtgaag tcttacaagg      240
ttatcttatt aataaaattc aaacatccta ggtaaaaaaa aaaaaaggtc agaattgttt    300
agtgactgta atttttcttt gcgcactaag gaaagtgcaa agtaacttag agtgactgaa    360
acttcacaga atagggttga agattgaatt cataactatc ccaaagacct atccattgca    420
ctatgcttta tttaaaaacc acaaaacctg tgctgttgat ctcataaata gaacttgtat    480
ttatatttat tttcatttta gtctgtcttc ttggttgctg ttgatagaca ctaaaagagt    540
attagatatt atctaagttt gaatataagg ctataaatat ttataatttt ttaaaatagt    600
attcttggta attgaattat tcttctgttt aaaggcagaa gaaataattg aacatcatcc    660 tgagttttt tgtaggaatc agagcccaat attttgaaac aaatgcataa tctaagtcaa    720
atggaaagaa atataaaaag taacattatt acttcttgtt ttcttcagta tttaacaatc    780
cttttttttc ttcccttgcc cagacaagag tgaggttgct catcggttta agatttggg    840 agaagaaaat ttcaaagcct tgtaagttaa aatattgatg aatcaaattt aatgtttcta    900
atagtgttgt ttattattct aaagtgctta tatttccttg tcatcagggt tcagattcta    960
aaacagtgct gcctcgtaga gttttctgcg ttgaggaaga tattctgtat ctgggctatc   1020
caataaggta gtcactggtc acatggctat tgagtacttc aaatatgaca agtgcaactg   1080
agaaacaaaa acttaaattg tatttaattg tagttaattt gaatgtatat agtcacatgt   1140
ggctaatggc tactgtattg gacagtacag ctctggaact tgcttggtgg aaaggacttt   1200
aatataggtt tcctttggtg gcttacccac taaatcttct ttacatagca agcattcctg   1260
tgcttagttg ggaatattta attttttttt tttttaaga cagggtctcg ctctgtcgcc   1320
caggctggag tgcagtggcg caatctcggc tcactgcaaa ctccgcctcc cgggttcacg   1380
ccattctcct gcctcagcct cccgagtagc tgggactaca ggcgcccgcc atcacgcccg   1440
gctaatcttt tgtattttta gtagagatgg ggtttcaccg tgtgccagga tggtctcaat   1500
```

```
ctcctgacat cgtgatctgc ccacctcggc ctcccaaagt gctgggatta caggagtgag    1560
ccaccgcgcc cggcctattt aaatgttttt taatctagta aaaatgaga  aaattgtttt    1620
tttaaaagtc tacctaatcc tacaggctaa ttaaagacgt gtgtggggat caggtgcggt    1680
ggttcacacc tgtaatccca gcactttgga aggctgatgc aggaggattg cttgagccca    1740
ggagttcaag accagcctgg gcaagtctct ttaaaaaaaa caaaacaaac aaacaaaaaa    1800
attaggcatg gtggcacatg cctgtagtcc tagctactta ggaggctgac gtaggaggat    1860
cgtttggacc tgagaggtca aggctacagt gagccatgat tgtgccactg cactccagcc    1920
tgggtgacag agtgagactc tgtctcaaaa aagaaaaagg aaatctgtgg ggtttgtttt    1980
agttttaagt aattctaagg actttaaaaa tgcctagtct tgacaattag atctatttgg    2040
catacaattt gcttgcttaa tctatgtgtg tgcatagatc tactgacaca cgcatacata    2100
taaacattag ggaactacca ttctctttgc gtaggaagcc acatatgcct atctaggcct    2160
cagatcatac ctgatatgaa taggcttct ggataatggt gaagaagatg tataaaagat    2220
agaacctata cccatacatg atttgttctc tagcgtagca acctgttaca tattaaagtt    2280
ttattatact acattttct acatcctttg tttcagggtg ttgattgcct ttgctcagta     2340
tcttcagcag tgtccatttg aagatcatgt aaaattagtg aatgaagtaa ctgaatttgc    2400
aaaaacatgt gttgctgatg agtcagctga aaattgtgac aaatcacttc atacccttt     2460
tggagacaaa ttatgcacag ttgcaactct tcgtgaaacc tatggtgaaa tggctgactg    2520
ctgtgcaaaa caagaacctg agagaaatga atgcttcttg caacacaaag atgacaaccc    2580
aaacctcccc cgattggtga ccagaggt tgatgtgatg tgcactgctt ttcatgacaa      2640
tgaagagaca ttttgaaaa  aatacttata tgaaattgcc agaagacatc cttactttta    2700
tgccccggaa ctccttttct ttgctaaaag gtataaagct gcttttacag aatgttgcca    2760
agctgctgat aaagctgcct gcctgttgcc aaagctcgat gaacttcggg atgaagggaa    2820
ggcttcgtct gccaaacaga gactcaagtg tgccagtctc caaaaatttg gagaaagagc    2880
tttcaaagca tgggcagtag ctcgcctgag ccagagattt cccaaagctg agtttgcaga    2940
agtttccaag ttagtgacag atcttaccaa agtccacacg gaatgctgcc atggagatct    3000
gcttgaatgt gctgatgaca gggcggacct tgccaagtat atctgtgaaa atcaagattc    3060
gatctccagt aaactgaagg aatgctgtga aaaacctctg ttggaaaat  cccactgcat    3120
tgccgaagtg gaaatgatg agatgcctgc tgacttgcct tcattagctg ctgattttgt    3180
tgaaagtaag gatgtttgca aaaactatgc tgaggcaaag gatgtcttcc tgggcatgtt    3240
tttgtatgaa tatgcaagaa ggcatcctga ttactctgtc gtgctgctgc tgagacttgc    3300
caagacatat gaaccactc  tagagaagtg ctgtgccgct gcagatcctc atgaatgcta    3360
tgccaaagtg ttcgatgaat ttaaacctct tgtggaagag cctcagaatt taatcaaaca    3420
aaattgtgag cttttgagc agcttggaga gtacaaattc cagaatgcgc tattagttcg    3480
ttacaccaag aaagtacccc aagtgtcaac tccaactctt gtagaggtct caagaaacct    3540
aggaaaagtg ggcagcaaat gttgtaaaca tcctgaagca aaagaatgc  cctgtgcaga    3600
agactatcta tccgtggtcc tgaaccagtt atgtgtgttg catgagaaaa cgccagtaag    3660
tgacagagtc accaaatgct gcacagaatc cttggtgaac aggcgaccat gcttttcagc    3720
tctggaagtc gatgaaacat acgttcccaa agagtttaat gctgaaacat tcaccttcca    3780
tgcagatata tgcacacttt ctgagaagga gagacaaatc aagaaacaaa ctgcacttgt    3840
```

-continued

```
tgagctcgtg aaacacaagc ccaaggcaac aaaagagcaa ctgaaagctg ttatggatga      3900
tttcgcagct tttgtagaga agtgctgcaa ggctgacgat aaggagacct gctttgccga      3960
ggagggtaaa aaacttgttg ctgcaagtca agctgcctta ggcttataac tcgag           4015
```

<210> SEQ ID NO 28
<211> LENGTH: 34
<212> TYPE: DNA
<213> ORGANISM: Artificial sequence
<220> FEATURE:
<223> OTHER INFORMATION: oligonucleotide

<400> SEQUENCE: 28

```
ataacttcgt ataatgtatg ctatacgaag ttat                                    34
```

<210> SEQ ID NO 29
<211> LENGTH: 34
<212> TYPE: DNA
<213> ORGANISM: Artificial sequence
<220> FEATURE:
<223> OTHER INFORMATION: oligonucleotide

<400> SEQUENCE: 29

```
tattgaagca tattacatac gatatgcttc aata                                    34
```

<210> SEQ ID NO 30
<211> LENGTH: 34
<212> TYPE: DNA
<213> ORGANISM: Artificial sequence
<220> FEATURE:
<223> OTHER INFORMATION: oligonucleotide

<400> SEQUENCE: 30

```
cacctttcgt ataatgtatg ctatacgaag ttat                                    34
```

<210> SEQ ID NO 31
<211> LENGTH: 3155
<212> TYPE: DNA
<213> ORGANISM: Artificial sequence
<220> FEATURE:
<223> OTHER INFORMATION: a sequence containing a mutant Loxp site, a
      wide type synthetic Loxp site, and neo and TK genes

<400> SEQUENCE: 31

```
cacctttcgt ataatgtatg ctatacgaag ttattaggtc tgaagaggag tttacgtcca        60
gccaagctag cttggctgca ggtcgagcag tgtggttttc aagaggaagc aaaaagcctc       120
tccacccagg cctggaatgt ttccacccaa tgtcgagcag tgtggttttg caagaggaag       180
caaaaagcct ctccacccag gcctggaatg tttccaccca atgtcgagca accccgccc        240 agcgtcttgt cattggcgaa ttcgaacacg cagatgcagt cggggcggcg cggtcccagg       300
tccacttcgc atattaaggt gacgcgtgtg gcctcgaaca ccgagcgacc ctgcagccaa       360
tatgggatcg gccattgaac aagatggatt gcacgcaggt tctccggccg cttgggtgga      420
gaggctattc ggctatgact gggcacaaca gacaatcggc tgctctgatg ccgccgtgtt       480
ccggctgtca gcgcaggggc gcccggttct ttttgtcaag accgacctgt ccggtgccct       540
gaatgaactg caggacgagg cagcgcggct atcgtggctg gccacgacgg gcgttccttg       600
cgcagctgtg ctcgacgttg tcactgaagc gggaagggac tggctgctat gggcgaagt        660 gccggggcag gatctcctgt catctcacct tgctcctgcc gagaaagtat ccatcatggc       720
tgatgcaatg cggcggctgc atacgcttga tccggctacc tgcccattcg accaccaagc       780
```

```
gaaacatcgc atcgagcgag cacgtactcg gatggaagcc ggtcttgtcg atcaggatga    840
tctggacgaa gagcatcagg ggctcgcgcc agccgaactg ttcgccaggc tcaaggcgcg    900
catgcccgac ggcgaggatc tcgtcgtgac ccatggcgat gcctgcttgc cgaatatcat    960
ggtgaaaat ggccgctttt ctggattcat cgactgtggc cggctgggtg tggcggaccg    1020
ctatcaggac atagcgttgg ctacccgtga tattgctgaa gagcttggcg gcgaatgggc   1080
tgaccgcttc ctcgtgcttt acggtatcgc cgctcccgat tcgcagcgca tcgccttcta   1140
tcgccttctt gacgagttct tctgagggga tcggcaataa aaagacagaa taaaacgcac   1200
gggtgttggg tcgtttgttc ggatccgtcg agcagtgtgg ttttcaagag gaagcaaaaa   1260
gcctctccac ccaggcctgg aatgtttcca cccaatgtcg agcagtgtgg ttttgcaaga   1320
ggaagcaaaa agcctctcca cccaggcctg gaatgtttcc acccaatgtc gagcaaaccc   1380
cgcccagcgt cttgtcattg gcgaattcga acacgcagat gcagtcgggg cggcgcggtc   1440
cgaggtccac ttcgcatatt aaggtgacgc gtgtggcctc gaacaccgag cgaccctgca   1500
gcgacccgct taacagcgtc aacagcgtgc cgcagatctt ggtggcgtga aactcccgca   1560
cctcttcggc cagcgccttg tagaagcgcg tatggcttcg taccccggcc atcaacacgc   1620
gtctgcgttc gaccaggctg cgcgttctcg cggccatagc aaccgacgta cggcgttgcg   1680
ccctcgccgg cagcaagaag ccacggaagt ccgcccggag cagaaaatgc ccacgctact   1740
gcgggtttat atagacggtc cccacgggat ggggaaaacc accaccacgc aactgctggt   1800
ggccctgggt tcgcgcgacg atatcgtcta cgtacccgag ccgatgactt actggcgggt   1860
gctgggggct tccgagacaa tcgcgaacat ctacaccaca caacaccgcc tcgaccaggg   1920
tgagatatcg gccggggacg cggcggtggt aatgacaagc gcccagataa caatgggcat   1980
gccttatgcc gtgaccgacg ccgttctggc tcctcatatc gggggggagg ctgggagctc   2040
acatgccccg cccccggccc tcaccctcat cttcgaccgc catcccatcg ccgccctcct   2100
gtgctacccg gccgcgcgt accttatggg cagcatgacc cccaggccg tgctggcgtt   2160
cgtggccctc atcccgccga ccttgcccgg caccaacatc gtgcttgggg cccttccgga   2220
ggacagacac atcgaccgcc tggccaaacg ccagcgcccc ggcgagcggc tggacctggc   2280
tatgctggct gcgattcgcc gcgtttacgg gctacttgcc aatacggtgc ggtatctgca   2340
gtgcggcggg tcgtgcgggg aggactgggg acagcttttcg gggacggccg tgccgcccca   2400
gggtgccgag ccccagagca cgcgggccc acgacccat atcggggaca cgttattacc   2460
ctgttcggcc ccccgagttg ctggcccca acggcgacct gtataacgtg tttgcctggg   2520
ccttggacgt cttggccaaa cgcctccgtt ccatgcacgt ctttatcctg gattacgacc   2580
aatcgcccgc cggctgccgg gacgccctgc tgcaacttac ctccgggatg gtccagaccc   2640
acgtcaccac ccccggctcc ataccgacga tatgcgacct ggcgcgcacg tttgcccggg   2700
agatggggga ggctaactga aacacggaag gagacaatac cggaaggaac ccgcgctatg   2760
acggcaataa aaagacagaa taaaacgcac gggtgttggg tcgtttgttc ataacgcgg    2820
ggttcggtcc cagggctggc actctgtcga taccccaccg agaccccatt ggggccaata   2880
cgcccgcgtt tcttcctttt ccccacccca cccccaagt tcgggtgaag gcccagggct   2940
cgcagccaac gtcgggcgg caggccctgc catagccact ggccccgtgg gttagggacg   3000
gggtccccca tggggaatgg tttatggttc gtgggggtta ttattttggg cgttgcgtgg   3060
gggtcaggtc cacgacccaa gctgcctcga ggaattccga tcatattcaa taaccttaa    3120
tataacttcg tataatgtat gctatacgaa gttat                              3155
```

<210> SEQ ID NO 32
<211> LENGTH: 3314
<212> TYPE: DNA
<213> ORGANISM: Artificial sequence
<220> FEATURE:
<223> OTHER INFORMATION: artificial human lactoferrin mini gene

<400> SEQUENCE: 32

| | | | | | |
|---|---|---|---|---|---|
| ctcgagatga | aacttgtctt | cctcgtcctg | ctgttcctcg | gggccctcgg | actgtgtctg | 60 |
| gctggccgta | ggagaaggag | tgttcagtgg | tgcaccgtat | cccaacccga | ggccacaaaa | 120 |
| tgcttccaat | ggcaaaggaa | tatgagaaga | gtgcgtggcc | ctcctgtcag | ctgcataaag | 180 |
| agagactccc | ccatccagtg | tatccaggcc | attgcggaaa | acagggccga | tgctgtgacc | 240 |
| cttgatggtg | gtttcatata | cgaggcaggc | ctggccccct | acaaactgcg | acctgtagcg | 300 |
| gcggaagtct | acgggaccga | aagacagcca | cgaactcact | attatgccgt | ggctgtggtg | 360 |
| aagaagggcg | gcagctttca | gctgaacgaa | ctgcaaggtc | tgaagtcctg | ccacacaggc | 420 |
| cttcgcagga | ccgctggatg | gaatgtccct | atagggacac | ttcgtccatt | cttgaattgg | 480 |
| acgggtccac | ctgagcccat | tgaggcagct | gtggccaggt | tcttctcagc | cagctgtgtt | 540 |
| cccggtgcag | ataaaggaca | gttccccaac | ctgtgtcgcc | tgtgtgcggg | gacaggggaa | 600 |
| aacaaatgtg | ccttctcctc | ccaggaaccg | tacttcagct | actctggtgc | cttcaagtgt | 660 |
| ctgagagacg | gggctggaga | cgtggctttt | atcagagaga | gcacagtgtt | tgaggacctg | 720 |
| tcagacgagc | tgaaaggga | cgagtatgag | ttactctgcc | cagacaacac | tcggaagcca | 780 |
| gtggacaagt | tcaaagactg | ccatctggcc | cgggtcccctt | ctcatgccgt | tgtggcacga | 840 |
| agtgtgaatg | gcaaggagga | tgccatctgg | aatcttctcc | gccaggcaca | ggaaaagttt | 900 |
| ggaaaggaca | agtcaccgaa | attccagctc | tttggctccc | ctagtgggca | gaaagatctg | 960 |
| ctgttcaagg | actctgccat | ggggtttcg | agggtgcccc | cgaggataga | ttctgggctg | 1020 |
| taccttggct | ccggctactt | cactgccatc | cagaacttga | ggaaaagtga | ggaggaagtg | 1080 |
| gctgccggc | gtgcgcgggt | cgtgtggtgt | gcggtgggcg | agcaggagct | gcgcaagtgt | 1140 |
| aaccagtgga | gtggcttgag | cgaaggcagc | gtgacctgct | cctcggcctc | caccacagag | 1200 |
| gactgcatcg | ccctggtgct | gaaaggagaa | gctgatgcca | tgagtttgga | tggaggatat | 1260 |
| gtgtacactg | caggcaaatg | tggtttggtg | cctgtcctgg | cagagaacta | caatcccaa | 1320 |
| caaagcagtg | accctgatcc | taactgtgtg | gatagacctg | tggaaggata | tcttgctgtg | 1380 |
| gcggtggtta | ggagatcaga | cactagcctt | acctggaact | ctgtgaaagg | caagaagtcc | 1440 |
| tgccacaccg | ccgtggacag | gactgcaggc | tggaatatcc | ccatgggcct | gctcttcaac | 1500 |
| cagacgggct | cctgcaaatt | tgatgaatat | ttcagtcaaa | gctgtgcccc | tgggtctgac | 1560 |
| ccgagatcta | atctctgtgc | tctgtgtatt | ggcgacgagc | agggtgagaa | taagtgcgtg | 1620 |
| cccaacagca | atgagagata | ctacggctac | actggggctt | ccggtgcct | ggctgagaat | 1680 |
| gctggagacg | ttgcatttgt | gaaagatgtc | actgtcttgc | agaacactga | tggaaataac | 1740 |
| aatgaggcat | gggctaagga | tttgaagctg | gcagactttg | cgctgctgtg | cctcgatggc | 1800 |
| aaacggaagc | ctgtgactga | ggctagaagc | tgccatcttg | ccatgccccc | gaatcatgcc | 1860 |
| gtggtgtctc | ggatggataa | ggtggaacgc | ctgaaacagg | tgctgctcca | ccaacaggta | 1920 |
| tggaccacag | gcttctagt | gctttcttag | ctgtgtgggc | tcatgttagg | tgaggagatc | 1980 |
| acagagctag | gtgcaccagc | ccactcgatc | ctctctagtc | ctctacttga | agctcatggt | 2040 |

```
gagagtattg gcttcatgct gtggcgttgc ccagagtgtc aacaagaaca acagaggctt     2100
ttgactctgg gctttctggg actcactcca tttctgctga gactctgtgc cctggccttg     2160
ttgccatcac tgcctggctc agaggctgtc ttttccctc ctgctgttct tctggcaaat      2220
gaggaagcca ctgagccttc ctcccacatg cattagtata gtgcttttta ctcaggtgac     2280
atttcctgaa cctgggccga gtgaacagtg ctctaggcca ggcctctaaa acagcaaact     2340
cagaaggtgc cctatagatt tagggctctc taaatgtgat ttgaacgaaa tcccaaaatt     2400
ttcttaaaat ctgggatttt attagaactt ctatttttat catataacat catgtctctg     2460
tgtgcttttg aagaaaacaa ctcaggaata acaagactgg ccaccataac tggcctttat     2520
ggagctctta acgtgcacac acagtggtgc tggtgagaga gctgccgtga ctgaggggtt     2580
tgggtctcag tctccccaca tgggagcctg gacagagca ggaactgtgt gagggaggca      2640
gggtgaccga cctgcacact gagctggtta gtggctgagc ctgggttttc ctagcagcct     2700
gcctctctag aagagctgca tattagaatg tcctgagcaa ttgacttgtg agggcagatc     2760
tcaaaacccc tccattgttg ccttgtcacc cataagaagt tgtatgggaa aaggtcacag    2820
gttaagaagg aaggaaagat ggcagatggt aggaggtagg accagaagtg gtgtgaggcc     2880
tggatgctgc ccaaggcggg cctgccacca ggagtgtggg gtgggggact ccactaagga    2940
ggtggaatga ctccagaact cagctccttc tgccccatgg ttttctcagg gctgttcttg    3000
ggtggaagaa ataccccttt gcctccttta acccataaat tcctcttttc cttagctact    3060
cactgtctgc ccttttgtcg caggctaaat ttgggagaaa tggatctgac tgcccggaca    3120
agttttgctt attccagtct gaaaccaaaa accttctgtt caatgacaac actgagtgtc    3180
tggccagact ccatggcaaa acaacatatg aaaaatattt gggaccacag tatgtcgcag    3240
gcattactaa tctgaaaaag tgctcaacct ccccccctcct ggaagcctgt gaattcctca   3300
ggaagtaact cgag                                                      3314

<210> SEQ ID NO 33
<211> LENGTH: 21
<212> TYPE: DNA
<213> ORGANISM: Artificial sequence
<220> FEATURE:
<223> OTHER INFORMATION: oligonucleotide

<400> SEQUENCE: 33
accagttagc taggtgggca t                                                 21

<210> SEQ ID NO 34
<211> LENGTH: 20
<212> TYPE: DNA
<213> ORGANISM: Artificial sequence
<220> FEATURE:
<223> OTHER INFORMATION: oligonucleotide

<400> SEQUENCE: 34
ggttttctca gggctgttct                                                   20

<210> SEQ ID NO 35
<211> LENGTH: 19
<212> TYPE: DNA
<213> ORGANISM: Artificial sequence
<220> FEATURE:
```

```
<223> OTHER INFORMATION: oligonucleotide

<400> SEQUENCE: 35
ttctgacact agcgccacc                                                  19

<210> SEQ ID NO 36
<211> LENGTH: 19
<212> TYPE: DNA
<213> ORGANISM: Artificial sequence
<220> FEATURE:
<223> OTHER INFORMATION: oligonucleotide

<400> SEQUENCE: 36
gccagctccc attagcttg                                                  19

<210> SEQ ID NO 37
<211> LENGTH: 20
<212> TYPE: DNA
<213> ORGANISM: Artificial sequence
<220> FEATURE:
<223> OTHER INFORMATION: oligonucleotide

<400> SEQUENCE: 37
gaagtctacg ggaccgaaag                                                 20

<210> SEQ ID NO 38
<211> LENGTH: 19
<212> TYPE: DNA
<213> ORGANISM: Artificial sequence
<220> FEATURE:
<223> OTHER INFORMATION: oligonucleotide

<400> SEQUENCE: 38
tagccggagc caaggtaca                                                  19

<210> SEQ ID NO 39
<211> LENGTH: 116
<212> TYPE: DNA
<213> ORGANISM: Artificial sequence
<220> FEATURE:
<223> OTHER INFORMATION: double Loxp sequence

<400> SEQUENCE: 39
agtgaattca taacttcgta taatgtatgc tatacgaaag gtggccgcgg gagtcgacca     60
tggcggccgc ctataacttc gtataatgta tgctatacga agttatgcaa gcttgg        116

<210> SEQ ID NO 40
<211> LENGTH: 192
<212> TYPE: DNA
<213> ORGANISM: Artificial sequence
<220> FEATURE:
<223> OTHER INFORMATION: sequence encoding salmon calcitonin

<400> SEQUENCE: 40
ctcgagatga aggtcctcat ccttgcctgt ctggtggctc tggccattgc acaccaccac     60
caccaccaca gaagaagaag aaagtgcagc aacctgagca cctgcgtgct gggcaagctg    120
agccaggagc tgcacaagct gcagacctac cccgtgacca caccggcag cggcacccc     180 ggctaactcg ag                                                        192
```